United States Patent [19]
Sarr et al.

[11] Patent Number: 5,231,675
[45] Date of Patent: Jul. 27, 1993

[54] SHEET METAL INSPECTION SYSTEM AND APPARATUS

[75] Inventors: Dennis P. Sarr, Kent; Joey J. H. Mullen, Seattle; Thomas W. Jurick, Kirkland, all of Wash.

[73] Assignee: The Boeing Company, Seattle, Wash.

[21] Appl. No.: 576,694

[22] Filed: Aug. 31, 1990

[51] Int. Cl.⁵ ............................................. G06K 9/00
[52] U.S. Cl. ................................... 382/8; 356/237; 358/106; 382/34
[58] Field of Search ............... 382/8, 46, 34; 358/101, 358/106, 107; 356/237

[56] References Cited

U.S. PATENT DOCUMENTS

| | | | |
|---|---|---|---|
| 3,636,513 | 1/1972 | Tisdale | 340/146.3 AC |
| 3,638,188 | 1/1972 | Pincoffs et al. | 340/146.3 AC |
| 4,007,440 | 2/1977 | Kono et al. | 340/146.3 AC |
| 4,056,716 | 6/1976 | Baxter et al. | 382/8 |
| 4,072,928 | 2/1978 | Wilder | 340/146.3 H |
| 4,242,662 | 12/1980 | Tsujiyama et al. | 340/146.3 H |
| 4,288,852 | 9/1981 | Holland | 364/508 |
| 4,435,837 | 3/1984 | Abernathy | 382/41 |
| 4,481,664 | 11/1984 | Linger et al. | 382/8 |
| 4,486,775 | 12/1984 | Catlow | 358/106 |
| 4,490,848 | 12/1984 | Beall et al. | 382/121 |
| 4,491,962 | 1/1985 | Sakou et al. | 382/50 |
| 4,545,069 | 10/1985 | Kermisch | 382/46 |
| 4,581,762 | 4/1986 | Lapidus et al. | 382/22 |
| 4,593,406 | 6/1986 | Stone | 382/44 |
| 4,596,037 | 6/1986 | Bouchard et al. | 382/8 |
| 4,623,256 | 11/1986 | Ikenaga et al. | 382/8 |
| 4,630,225 | 12/1986 | Hisano | 364/559 |
| 4,658,428 | 4/1987 | Bedros et al. | 382/30 |
| 4,672,678 | 6/1987 | Koezuka et al. | 382/30 |
| 4,706,296 | 11/1987 | Pedotti et al. | 382/42 |
| 4,790,023 | 12/1988 | Matsui et al. | 382/8 |
| 4,975,863 | 12/1990 | Sistler et al. | 358/101 |
| 5,012,523 | 4/1991 | Kobayashi et al. | 382/8 |

OTHER PUBLICATIONS

Terry Lawhead, "Machine Visions", Seattle Times, Sep. 4, 1989, pp. D1, D4.
A. Papoulis, "Probability, Random Variables, and Stochastic Processes, 2.ed.", 1984, pp. 153-155.
Ballard & Brown, "Computer Vision", 1982, p. 255.

Primary Examiner—Leo H. Boudreau
Attorney, Agent, or Firm—Dellett, Smith-Hill and Bedell

[57] ABSTRACT

An apparatus for inspecting sheet metal parts includes a computer for comparing a master representation to an inspected part. A part is scanned by passing the part in front of a computer vision system and an approximation of the part is thereby generated for comparison with the stored representation of a master part. The comparison includes checking for distance tolerances and proper feature placement of the scanned part and an inspection report for each inspected part is generated, indicating part acceptance status. Part tolerances may be varied for different parts and a library of parts may be consulted to automatically select an appropriate master part for comparison purposes.

25 Claims, 27 Drawing Sheets

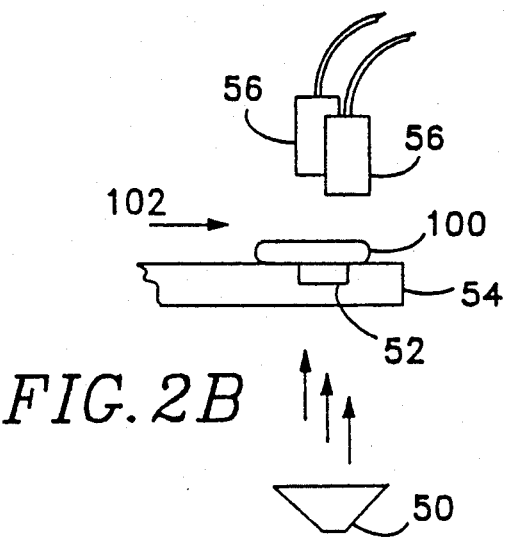
*FIG. 2B*
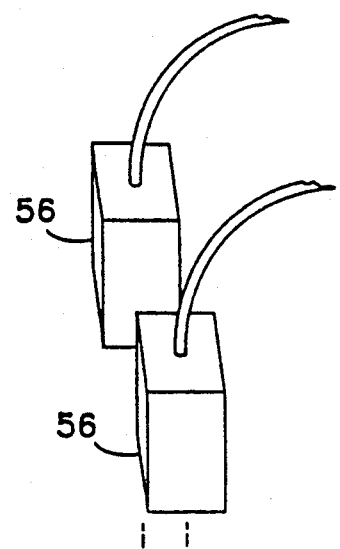
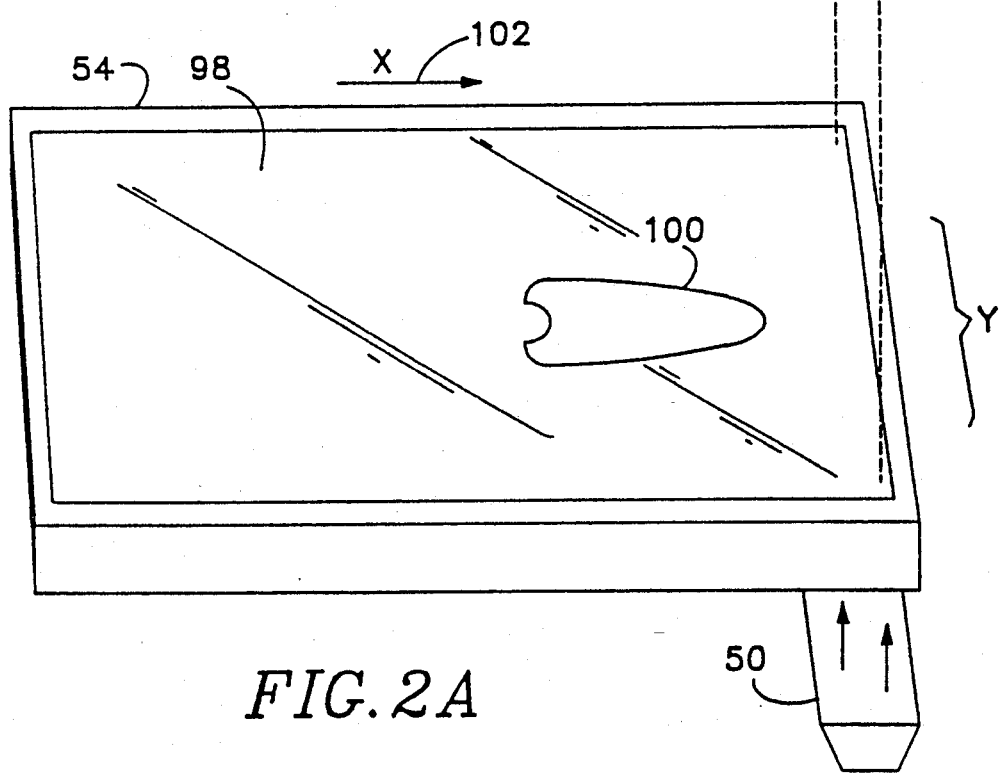
*FIG. 2A*

SHEET METAL INSPECTION SYSTEM AND APPARATUS

BACKGROUND OF THE INVENTION

The present invention relates to a computer vision inspection system and more particularly to a computer vision inspection system for sheet metal parts.

In manufacturing operations, a wide variety of sheet metal parts are required and need to be inspected to determine whether they are within acceptable error tolerances. Different parts may have different error tolerances associated therewith requiring different inspection criteria. Past methods of inspection have included the statistical sampling of parts from a manufacturing run and the determination of the occurrence of error for the entire run based on such a sample. Obviously this method has drawbacks in that a defective part may slip past the inspection process.

Inspection has typically involved selecting a part to be inspected and manually comparing the part with a template representing the desired shape. Such an inspection method is labor intensive and requires that a number of templates be maintained on hand to facilitate inspection. Other inspection methods merely involve comparison with engineering drawings.

While machine vision inspection systems have heretofore been designed to inspect large quantities of identical parts on an assembly line, in some industries manufacturing flow is not suited to such an arrangement. Machine vision systems as heretofore designed are not suited to a relatively low part quantity inspection wherein it is desired to inspect a wide variety of parts and to switch between part inspection types with relative ease.

A method which has been used to avoid massive template storage involves storing template information in a computer and generating a new inspection template when needed by means of a plotter and a mylar plotting surface. When a part is to be inspected, a new template is generated on mylar, but once the inspection is complete the mylar template is thrown away. Such a system has drawbacks in that it is wasteful and slow, with additional operations and personnel being required to generate the various templates.

Automated manufacturing processes often generate sheet metal parts from digital data created by a computer aided design process and there may be no template as such readily available. It would be desirable to provide an inspection method which quickly inspects parts using the design data from a computer aided design representation of a part.

SUMMARY OF THE INVENTION

In accordance with the present invention, in a particular embodiment thereof, machine vision sheet metal inspection includes generating a representation of a sheet metal part by placing the part to be inspected on a transparent back lighted table and scanning the part by moving the part along one axis in front of video camera means. The representation thus derived is used to determine the major and minor axes of the scanned part as well as the angle of orientation of the major axis. The generated part representation is rotated so as to have an angle of orientation identical to the angle of orientation of a stored master data set, where the master data set has been generated by a computer aided design system, or from actual scan data from a correctly dimensioned part previously placed on the scan table. The master and scanned part are compared and an acceptance report is generated indicating whether various features of the scanned part are within tolerance while also indicating the addition of extra or unwanted features as well as the absence of desired features.

It is accordingly an object of the present invention to provide improved inspection of sheet metal parts and the generation of acceptance data based thereupon.

It is another object of the present invention to utilize computer aided design information as an inspection template for performing a visual inspection of a sheet metal part.

It is another object of the present invention to enable multiple parts to be inspected in a rapid manner without requiring inspected parts to be precisely oriented on the inspection surface.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DRAWINGS

FIG. 2A is a perspective view of the sheet metal inspection system of the present invention;

FIG. 2B is a cross sectional view of the scanning system along the X-axis of the scan table;

DETAILED DESCRIPTION

Figure 1:
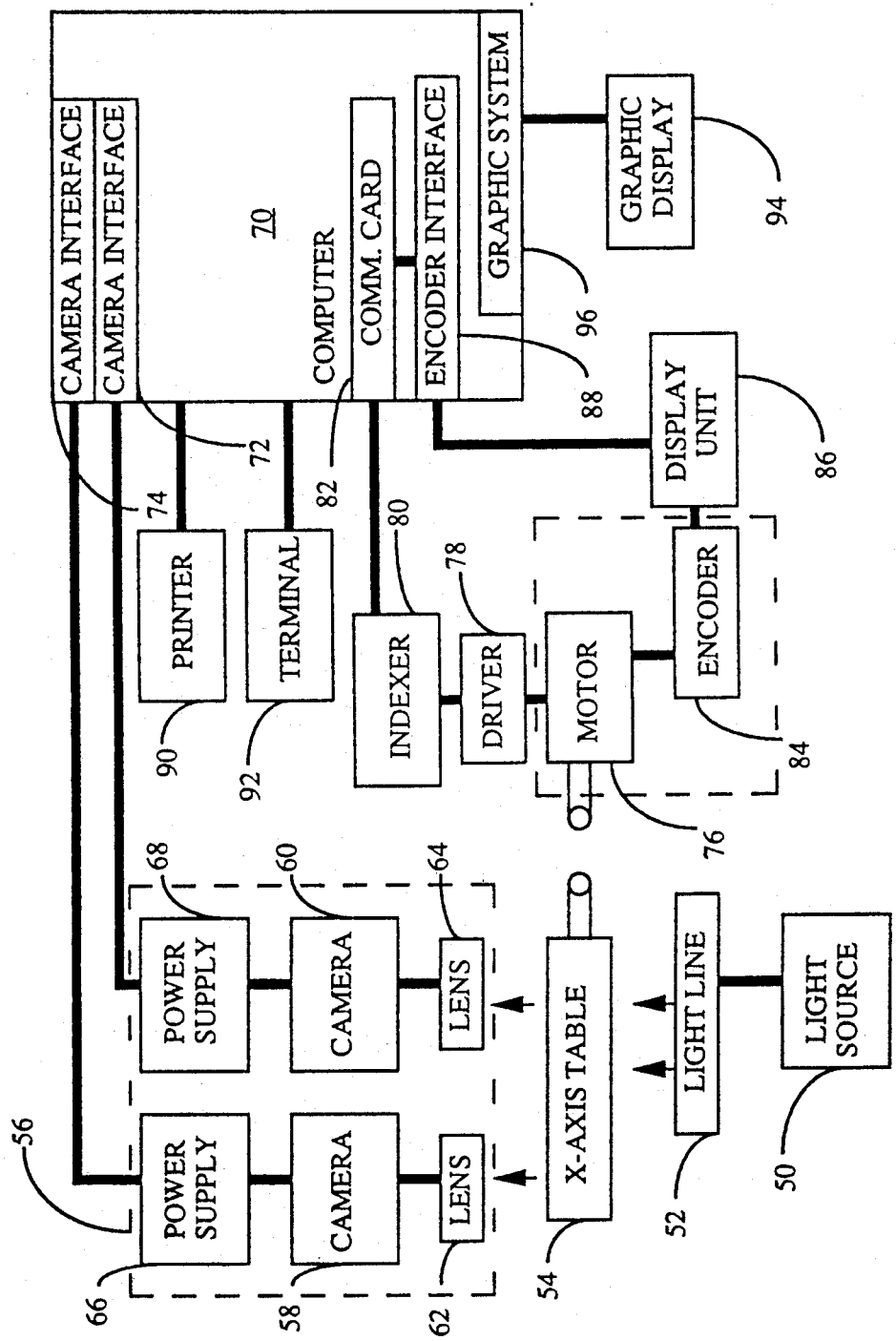
FIG. 1 is a block diagram of a particular embodiment of the present invention.

Referring to FIG. 1, a machine vision sheet metal inspection system includes a light source 50 which supplies light for "light line" 52. In a one embodiment, light source 50 consists of three Volpi cold light sources, 150 watt Intralux 6000, Volpi part number 23537. A line of light 52 is provided by Volpi part number 11734.001, the latter being constructed from fiber optic means connected to the source 50. Light line 52 is located beneath the surface of X-axis table 54 which is transparent or translucent whereby the light from the light line is transmitted through the surface to visual acquisition hardware 56 mounted above the table for receiving the light. Visual acquisition hardware comprises two cameras 58 and 60, two camera lenses 62 and 64 attached thereto, and the associated power supplies In a preferred embodiment, cameras 58 and 60 were Reticon line scan cameras model LC0120 with RL2048H camera sensors, lenses 62 and 64 were model CX100-135U and camera power supplies 66 and 68 were models RS0600. The sensor for each camera provides a 2,048 by 1 pixel array. The data output from the visual hardware 56 is supplied to a computer system 70 via an interface which in a preferred embodiment comprised a pair of Reticon SB6024 camera interface boards 72 and 74. The computer system 70 uses a multibus system, preferably comprising an 80386 Intel based system with four megabytes of random access memory, an Intel 80387 coprocessor, and a hard disk storage system. Since the Reticon camera interfaces 72 and 74 are designed for a one megabyte maximum memory system, the interface boards were modified to place them above the installed memory and avoid memory fragmentation problems. Although two cameras were utilized in the preferred embodiment, a wider scan field could be realized by increasing the number of cameras.

Referring again to X-axis table 54, preferably a model HMP-240 from DCI Corporation, the table is powered by motor 76 which operates to move the translatable surface of the table. The motor 76 is driven by motor driver 78 controlled by motor controller 80. Controller 80 is interfaced with computer system 70 via a communications card 82 suitably comprising an Intel SBC534 card operating a serial link at 9600 Baud. The controller 80 is preferably a Compumotor Indexer model 2100-1-P-488 with display unit model 721. The motor speed is variable, and may be set via an operator console to optimize results. Motor 76 is provided with a shaft encoder 84 connected to display unit 86 for indicating the position of motor 76 wherein the motor and shaft encoder 84 are an assembly preferably comprising Compumotor part number M57-102E. Display unit 86 provides the shaft encoder signal to computer system 70 via communications card 82 by way of shaft encoder interface 88. The display unit was tapped to acquire the shaft encoder signal, and the acquired signals were buffered to RS-422 signal levels for transfer to the computer system multibus via twisted wire pairs with a ground shield. This signal is received by communications card 82 and TTL buffered where the shaft encoder counts are totaled using a programmable counter/timer, e.g., an Intel type 8253. The count thus produced is read via normal polling software methods.

Other components of the inspection system include a printer 90, a computer terminal 92, and a graphics display 94 which includes a graphics subsystem 96. In a preferred embodiment graphics subsystem 96 was a Matrox MG-1280/8 graphics subsystem controlling graphics display 94, a Mitsubishi C-9920 PBK/WC color monitor. Computer terminal 92 was a C. Itoh CIT-224 terminal connected via a RS-232 interface, while line printer 90 was attached to a Centronics parallel interface of computer system 70. The latter may comprise any dot matrix type printer.

Referring now to FIG. 2A, a perspective view of the scanning system, and to FIG. 2B, a cross sectional view along the X-axis of the scan table, the general operation of the invention will be described. Inspection table 54 includes a clear or translucent portion 98 upon which a part to be inspected 100 is placed. While a single part 100 is illustrated in FIG. 2, the system is such that a number of parts may be placed on the inspection table 54 and an inspection performed on multiple parts at one time. Also, the parts may be randomly placed upon the inspection surface, i.e. no specific orientation need be observed. Light from source 50 located beneath the table is translated into a line of light beneath one end of table 54. The visual system 56 is oriented in a direction normal to the plane of table 54, directly above the line of light 52, with the table disposed therebetween. The line of light 52 extends across table 54 in the Y direction for providing a Y-axis view of the table for the visual system 56.

In operation, the table is moved across the field of view of the cameras in the X direction indicated by arrow 102 (by means 76, FIG. 1) for generating sequential scan lines, each scan line representing a single "X" value and a plurality of "Y" values. The X value is read by the system via shaft encoder 84, encoder display 86, interface 88 and communications card 82 of computer system 70 shown in FIG. 1. The process of moving the table and the part located thereupon across the field of view, while reading the X value, builds up a matrix of scan information representing the X and Y values available.

Figure 3:
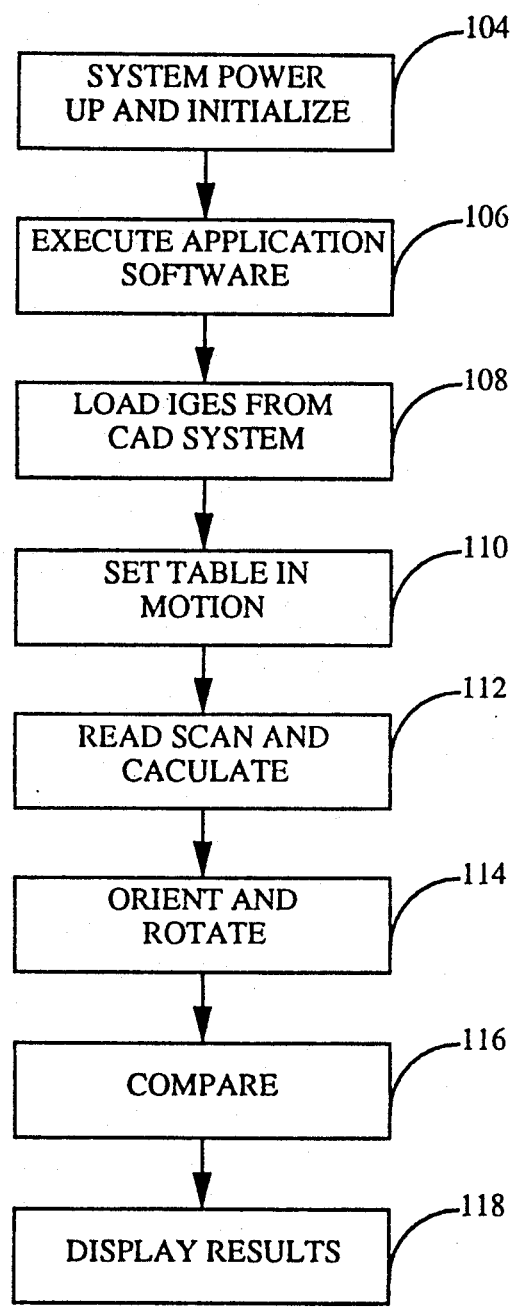
FIG. 3 is a flow chart of the overall steps performed in operation of the inspection system.

Referring now to FIG. 3, the general overall operation of the system will be further discussed. The system is initially powered up and initialized (step 104) and the scan software is executed (step 106). The master part digital data is loaded (as available) at step 108. In the preferred embodiment of the invention, this data is provided in IGES format (Initial Graphic Exchange Standard) from a computer aided design representation of the master part. Next, the system begins scanning a part to be inspected by setting the scan table in motion (step 110). Once the table is set in motion the system will read run length encoded data from the cameras and the respective shaft encoder position (step 112) to acquire the scan data. The typical scan rate in one embodiment of the invention was 200 scans per second. While the data is being collected, the centroid and major and minor axes of each scanned part are calculated concurrently as will be discussed hereinafter in greater detail. Once the parts have been scanned, the angle of orientation of the major axis of each part is calculated (step 114) and the part information is "rotated" to have a zero degree orientation. The scanned part information is then compared with the stored master part (step 116). If no master part data exists, the initial scan data can be used to generate part data.

The comparison step includes determining whether the scanned part shape matches the shape of the master part to within a desired tolerance (which may be set at the operator console), insuring that all holes present in the master part are also present in the scanned part and that the centers of all scanned holes are located in the proper position, and further, the scanned part is inspected to insure that no holes are present which are not present in the master. The results of the comparison are displayed (step 118), for example, on a graphics display, and may also be sent to a printer or other report generating device.

Figure 4A:
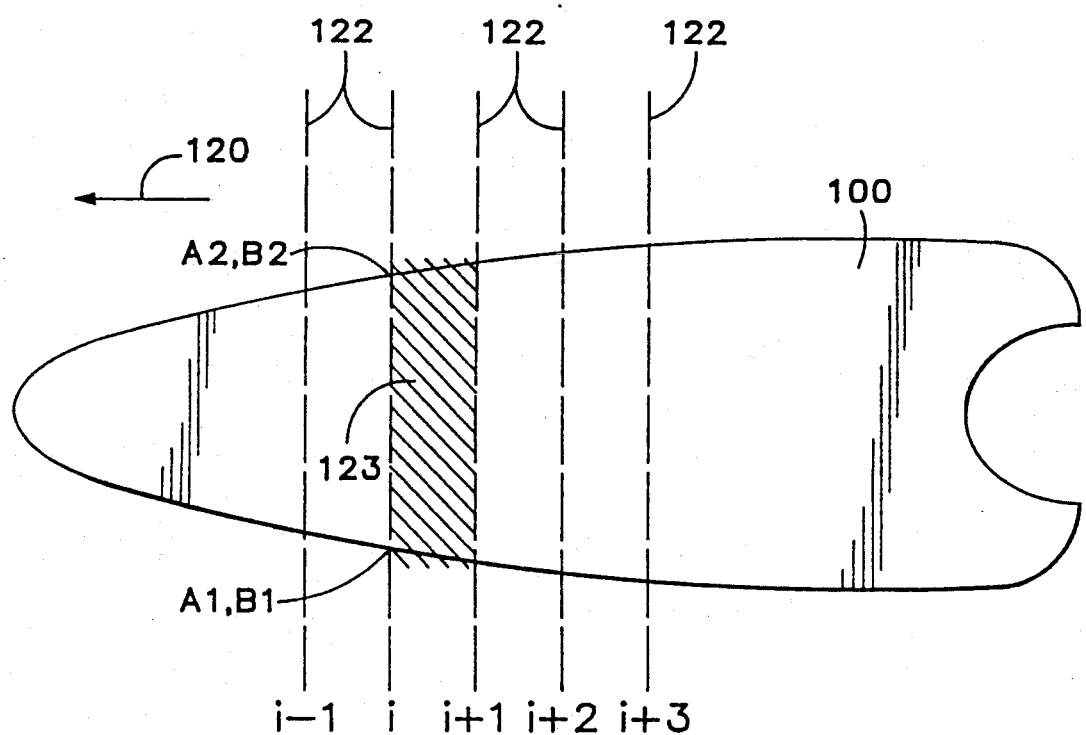
FIG. 4A is an illustration of the approximations made while scanning a part.
Figure 4B:
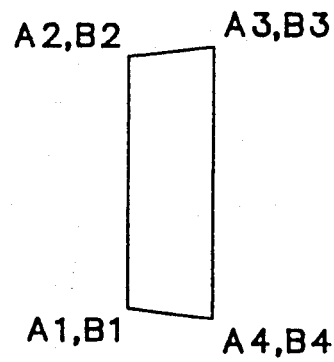
FIG. 4B illustrates a trapezoidal scan area.
Figure 4C:
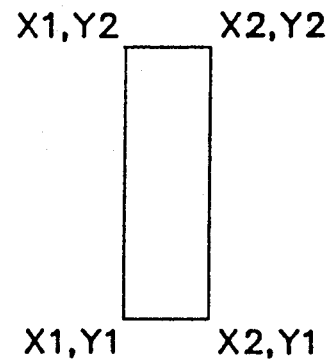
FIG. 4C illustrates a rectangular approximation of a trapezoidal scan area.

The scanning process will be better understood by referring to FIGS. 4A, 4B and 4C which illustrate the scanning of a representative part. The part 100 as viewed by the cameras (disposed normal to the plane of the part) passes before the field of view of the cameras in the direction of arrow 120, the latter representing the X direction of scanning. The camera generates each scan line 122 in the Y direction which constitutes discrete views of the part. These scan lines are correlated with the shaft encoder output so as to relate X and Y values of the scanned part. Since the scanned part is back lighted, the image presented to the cameras will consist of light and dark areas whereby the part outline is defined by transitions from light-to-dark and dark-to-light. When a part edge is first encountered, a transition along the Y-axis will occur, and the opposite edge of the part will produce a reverse transition.

The run length encoded data returned by the cameras indicates the pixel position at which each transition occurred and whether the transition was light-to-dark or dark-to-light. The information is used to select an appropriate value from a calibration array as discussed hereinafter with reference to FIG. 10. Two consecutive scan lines in a preferred embodiment are typically 0.003 inches apart, and the part is represented by a series of rectangular approximations wherein each approximation is defined by two scan lines. Five scan lines, i−1, i, i+1, i+2 and i+3, are illustrated in FIG. 4A, scan line i having a light-to-dark transition at the point $(A_1,B_1)$ and a dark-to-light transition at the point $(A_2,B_2)$. The scan lines i and i+1 of FIG. 4B define a trapezoidal slice 123 of part 100 having the coordinates $(A_1,B_1)$, $(A_2,B_2)$, $(A_3,B_3)$, and $(A_4,B_4)$. The area of this trapezoid is approximated by the rectangular box of FIG. 4C having corners $(X_1, Y_1)$, $(X_1, Y_2)$, $(X_2, Y_1)$ and $(X_2, Y_2)$, where $X_1=(A_2+A_1)/2$; $X_2=(A_4+A_3)/2$; $Y_1=(B_1+B_4)/2$; and $Y_2=(B_2+B_3)/2$. The centroid of the rectangle thus defined may be determined as follows.

$$Area = (X_2-X_1)*(Y_2-Y_1)$$

$$S_x = ((X_1+X_2)/2)*Area$$

$$S_y = ((Y_1+Y_2)/2)*Area$$

$S_x$ and $S_y$ represent the first-order moments of the rectangle and the centroid coordinate $(C_x,C_y)$ of an individual box may be determined by:

$$C_x = SX/Area$$

$$C_y = SY/Area.$$

The calculations of Area $(A_i)$, SX $(SX_i)$, SY $(SY_i)$, $C_x$ $(C_{xi})$ and $C_y$ $(C_{yi})$ may be generalized for an individual scan line i wherein $$A_i = (X_{i+1}-X_i)*(Y_{i+1}-Y_i)$$

$$SX_i = ((X_i+X_{i+1})/2)*A_i$$

$$SY_i = ((Y_i+Y_{i+1})/2)*A_i$$

$$CX_i = SX_i/A_i$$

$$CY_i = SY_i/A_i$$

Calculating the individual area, and SX and SY for each of n total scan lines allows the X and Y value of the centroid of the entire part to be calculated. The area of the part, PA=the summation for i=1 to n of $A_i$; PX=the summation of i=1 to n of $SX_i$; and PY=the summation for i=1 to n of $SY_i$. The X value of the centroid of the part is calculated as $$CX = PX/PA$$

and the Y value of the centroid is calculated as $$CY = PY/PA.$$

It will be noted that the centroid of the scanned part is calculated as the part is scanned.

A next step in the process is to determine the orientation of the part so as to allow part rotation and alignment of the major axis of the part to 0°. The orientation angle theta may be determined from the second-order moments of the part in conjunction with the following formula:

$$theta = (\tan^{-1}(2M_{11}/(M_{20}-M_{02})))/2 + n(pi/2)$$

where $M_{20}$, $M_{11}$ and $M_{02}$ are the second-order moments. (See Ballard & Brown, "Computer Vision" 1982 p. 255.) If n=2, n(pi/2)=180°. The second-order moments of each part are calculated by the joint probability density $M_{ij}$ $$M_{ij} = \int_{-\infty}^{\infty} \int_{-\infty}^{\infty} x^i y^j p(x,y) dx dy$$

$$M_{20} = \int_{-\infty}^{\infty} \int_{-\infty}^{\infty} x^2 p(x,y) dx dy$$

$$M_{02} = \int_{-\infty}^{\infty} \int_{-\infty}^{\infty} y^2 p(x,y) dx dy$$

-continued
$$M_{11} = \int_{-\infty}^{\infty} \int_{-\infty}^{\infty} xyp(x,y)dxdy$$

(See Papoulis, "Probability, Random Variables, and Stochastic Processes, 2ed.", 1984 pp. 153-155.)

These integrals, are approximated in the following manner. Oriented sums of X, Y and XY ($OSX_i$, $OSY_i$ and $OXY_i$ respectively) are calculated according the following formulas:

$$OSX_i = [[((X_i + X_{i+1})^2/4) * (X_{i+1} - X_1)] +$$
$$[((X_{i+1} - X_i) - 1) * (X_{i+1} - X_i) *$$
$$((X_{i+1} - X_i) + 1)]/12] * (Y_{i+1} - Y_i)$$
$$OSY_i = [[((Y_i + Y_{i+1})^2/4) * (Y_{i+1} - Y_i)] +$$
$$[((Y_{i+1} - Y_i) - 1) * (Y_{i+1} - Y_i) *$$
$$((Y_{i+1} - Y_i) + 1)]/12] * (X_{i+1} - X_i)$$
$$OXY_i = (X_{i+1} - X_i) * (Y_{i+1} - Y_i) *$$
$$((X_i + X_{i+1})/2) * ((Y_i + Y_{i+1})/2)$$

For an individual rectangle, these formulas correspond to the following:

$$OSX_i = [(C_x)^2 * dX + [(dX - 1) * dX * (dX + 1)]/12] * dY$$
$$OSY_i = [(C_y)^2 * dY + [(dY - 1) * dY * (dY + 1)]/12] * dX$$
$$OXY_i = dX * dY * C_x * C_y$$

where dX represents the X-axis width of the rectangle, dY represents the Y-axis width of the rectangle, and $C_x$, $C_y$ represent the X and Y values of the centroid of the rectangle.

Each of the oriented sums is translated to the origin by using the centroid of the parts as previously calculated. The translation is accomplished by subtracting the respective X and Y centroid values from each of the X and Y terms. For example, the formula $OXY_i$ would read as follows with translation included:

$$OXY_i = ((X_{i+1} - CX_i) - (X_i - CX_i)) *$$
$$((Y_{i+1} - CY_i) - (Y_i - CY_i)) *$$
$$(((X_i - CX_i) + (X_{i+1} - CX_i))/2) *$$
$$(((Y_i - CY_i) + (Y_{i+1} - CY_i))/2)$$

As each of the oriented values is calculated, it is accumulated in a sum. The part oriented X values, POX = summation for i=1 to n of $OSX_i$, the part oriented Y sum, POY = summation for i=1 to n of $OSY_i$ and the part XY sum, PXY = summation for i=1 to n of $OXY_i$ are calculated. It may then be noted that $PXY^2 = M_{11}$, $POX^2 = M_{20}$ and $POY^2 = M_{02}$ and the major axis of orientation of the part may then be determined from the following formula:

Orientation Angle (OA) = 180°
$-(\tan^{-1}(2*PXY^2/(POX^2 - POY^2)))/2$

Figure 9:
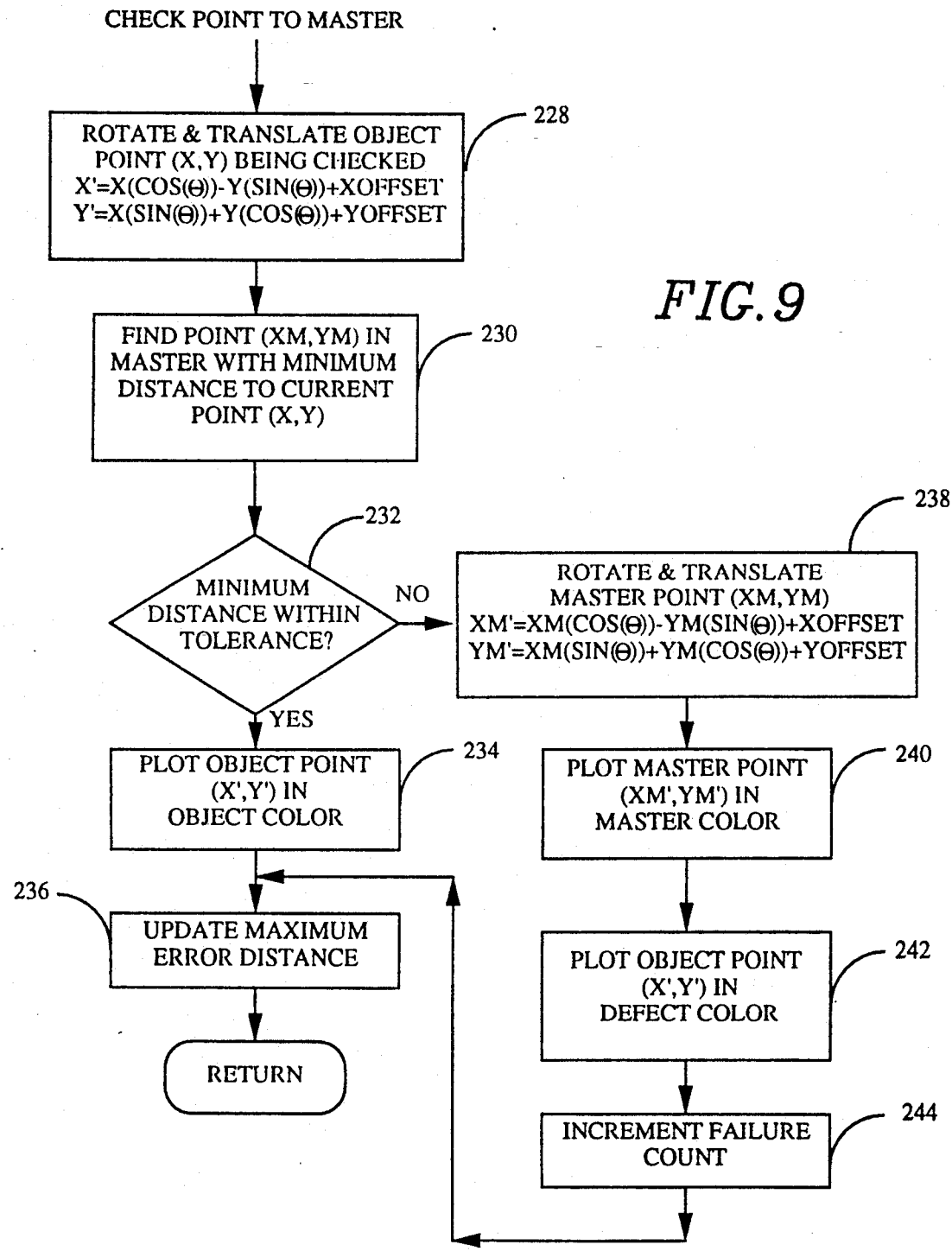
FIG. 9 is a more detailed flow chart of the individual point checking process of FIG. 7 and FIG. 8.

Having determined the orientation angle it is then possible to rotate the scanned part to align its major axis with the major axis of the master part for comparison and discussed further in connection with FIG. 9.

Figure 5:
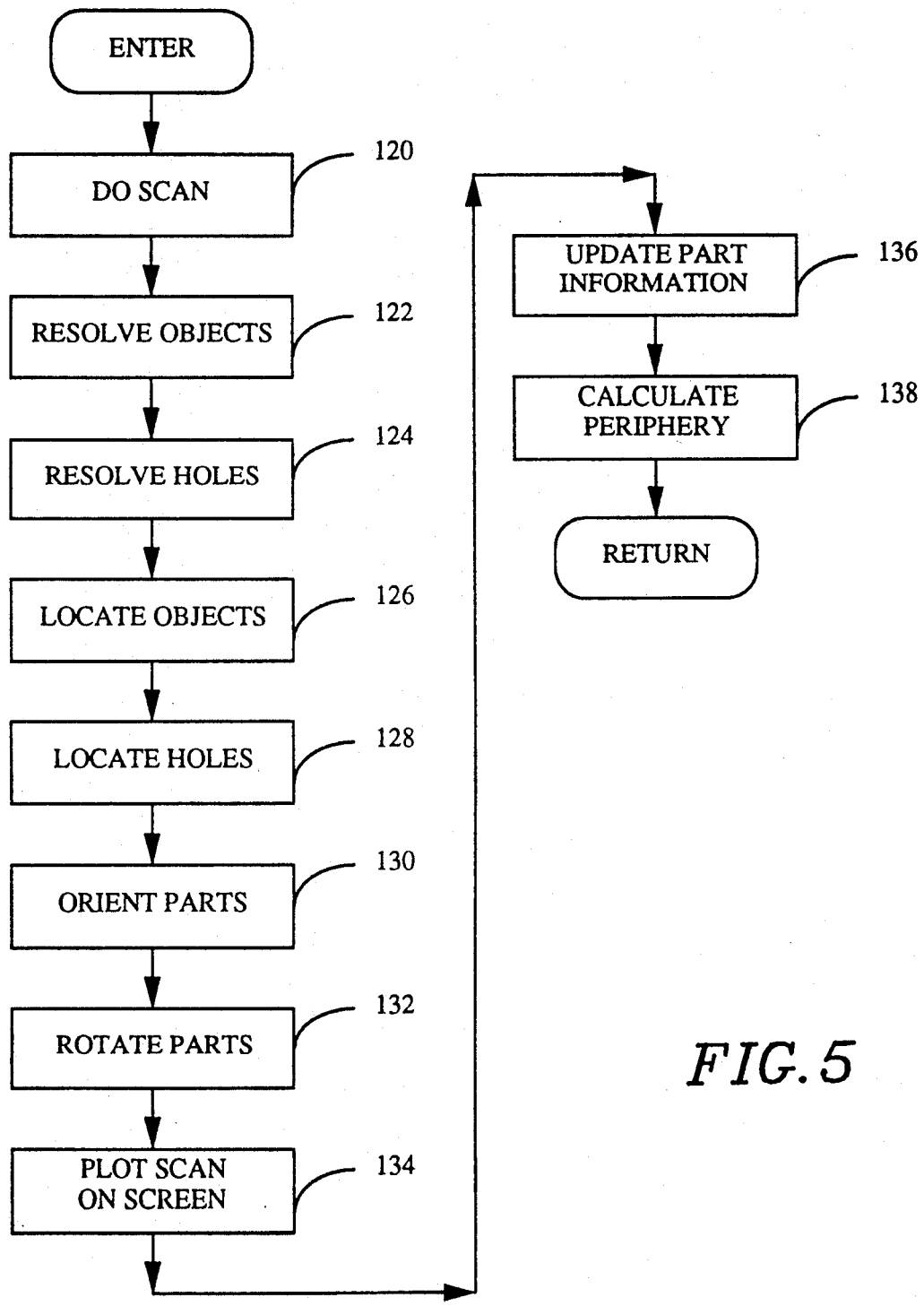
FIG. 5 is a flow chart of the overall scanning and plotting process of the present invention.

Referring now to FIGS. 5-26, the operational software of the present invention will be discussed. FIG. 5 is a flowchart showing the steps performed in the scan part and plot operation. The scan operation begins with the "do scan" process (step 120) which does the actual scanning of the part as discussed in greater detail with reference to FIG. 6A. During the scan process, located objects and holes are assigned labels and may be labeled more than once. Therefore, when the scan is completed, the objects picked up by the scan are resolved (step 122) wherein the object labels are reduced to the smallest common label; similarly in step 124, the holes within objects from the scan are resolved wherein the hole labels are reduced to the smallest common label. The resolve processes insure that a single label is assigned to each distinct object or hole. Next "locate objects" 126 is performed wherein the centroid of each object from the scan is calculated using the method described hereinabove. Similarly step 128 locates holes wherein the centroids of the holes of any object from the scan are calculated. Next, step 130 calculates the angle of orientation of each part, the parts located by the scan are then rotated in the "rotate parts" step 132, the parts as currently scanned are plotted on the screen (step 134), and the part information is updated (step 136) wherein information about each of the parts located during the scan is computed and tallied. The process then calculates the periphery of the located parts (step 138) wherein the periphery of the part is linked in a manner similar to connecting dots so that the part may be accessed via its periphery rather than via scan line information. This step is described in more detail in conjunction with FIG. 6B. After performing step 138, the scan and plot operation is complete.

Figure 6A:
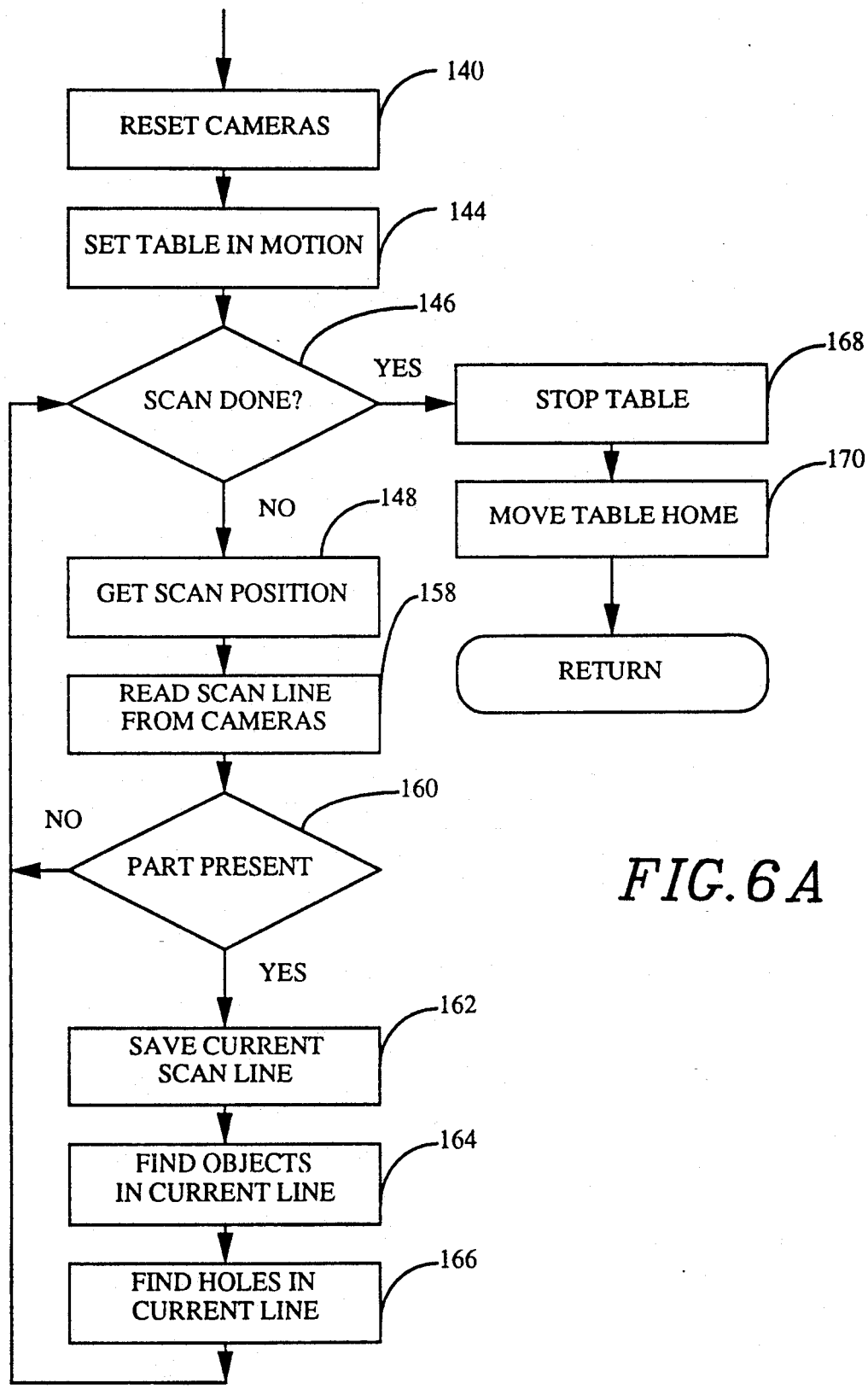
FIG. 6A is a more detailed flow chart of the scan portion of FIG. 5.

Referring now to FIG. 6A, the "do scan" block 120 of FIG. 5 will be described in greater detail. The initial process performed is the "reset cameras" step 140 wherein the video cameras are initialized to a known state, whereupon the scan table is set in motion (step 144). Decision block 146 then determines whether the scan has finished, which will occur when the end of the scan table is reached. If the result of decision block 146 is that the scan is not finished, then the process will enter process block 148 wherein the scan position is retrieved from the shaft encoder 84 of FIG. 1, the current scan line is read from the camera (step 158) and decision block 160 is entered wherein the current scan line is checked to determine if a part is present in that scan line. If no such part is present, there is no need to save the data from this scan line; therefore, the process will loop back to decision block 146 wherein the process determines if the scanning is finished.

If the scanning is not yet finished the process continues as discussed hereinabove. If the result of decision block 160 indicates that a part is present on the current scan line, process step 162 is executed wherein the current scan line is saved in computer memory and the objects in the current line are found (step 164) and the holes in the current scan line are also found (step 166). The "find objects" and "find holes" processes are similar and are described in greater detail herein with reference to FIGS. 13 and 14. Next, the process loops back to decision block 146 and the processor determines whether or not the current scan is finished. If the results of decision step 146 indicate that the scan is not done, the process will continue looping through acquiring scan data and finding objects and holes in the acquired scan data until the scan is finished. Once the decision block 146 determines that the scan is done, then the scan table is stopped (block 168), the scan table is moved home (step 170) wherein home indicates that the table is moved back to its starting position and the process then returns to continue execution as described in conjunction with FIG. 5. Once the part has been scanned and the data derived therefrom processed in accordance with the steps described, the scanned parts may be checked against a master part.

When scanning parts on systems with multiple cameras, there will typically be an overlap in the field of view of adjacent cameras thereby creating the need for splicing the overlapped scan areas into a single set of scan values. This is accomplished in the "read scan line from camera" process step 158 by stepping along in the array of scanned values until an overlap is encountered, and averaging the values from the two camera overlaps and leaving the average value as the scan value.

Figure 6B:
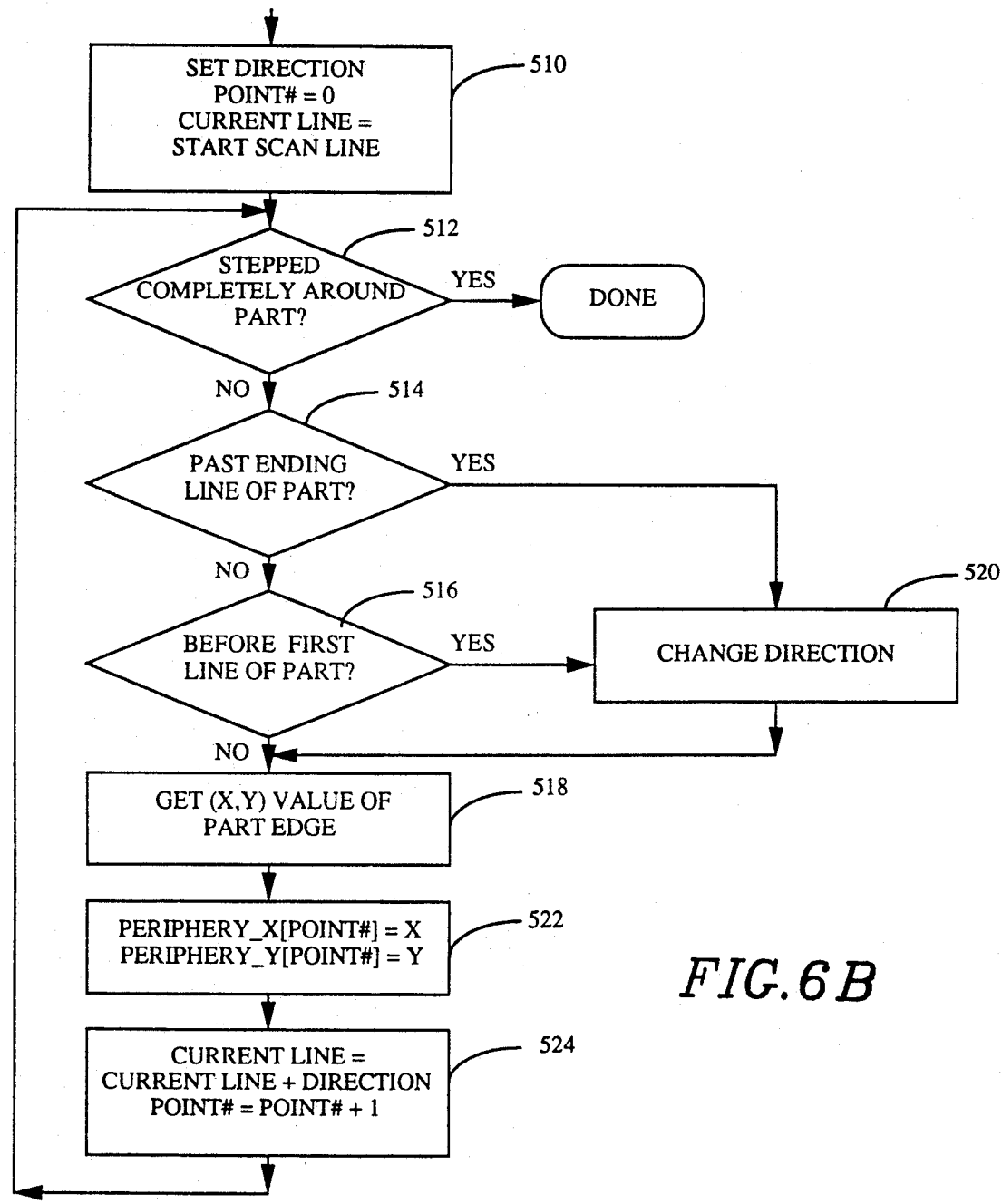
FIG. 6B is a more detailed flow chart of the periphery calculation of FIG. 5.

The process of calculating the periphery of a part (or holes) is described in greater detail in FIG. 6B. The process involves stepping along the edge or periphery of an individual part point-by-point, storing the X-axis and Y-axis values of each point in an array. Then, when two parts are compared, the comparison routine is able to step around the edge of the parts point-by-point, determining whether there is a match between the two parts. The process begins by initializing various items: DIRECTION, an indicator of the direction in which the process is stepping around the part, is set to an initial value, POINT NUMBER is set to zero, and CURRENT LINE, an indicator of the current scan line which is being examined, is set to the starting scan line of the current part (block 510). Next, decision block 512 is entered wherein the process determines whether the part edge has been completely stepped around and if so, the process is completed. However, if the part has not yet been completely traversed, decision block 514 determines whether the process has stepped beyond the last line of the current part. If the ending line has not been passed, the process enters decision block 516 to determine whether the process has stepped before the first line of the current part. The process will continue with step 518, obtaining the (X,Y) value of the part edge on the current line if decision block 516 indicates that the process is not before the first edge of the part. In both decision blocks 514 and 516, if the process has stepped beyond the bounds of the current part, then step 520 is performed wherein the direction of stepping is changed. The process then continues with step 518. In any event, the process next continues with step 522 wherein the X-axis and Y-axis values of the part edge are stored in two arrays; the X value is stored in PERIPHERY_X[] and the Y value is stored in PERIPHERY_Y[]. POINT NUMBER is used to map the values into unique locations of the periphery arrays for unique values of POINT NUMBER. Next, the process enters block 524, adding DIRECTION to CURRENT LINE and incrementing POINT NUMBER. The process then loops back to decision block 512, continuing execution until the part has been completely stepped around. In this manner, the process is able to step along the edge of the part in the X-axis direction, obtaining the Y-axis values of one edge of the part until the furthest X-axis edge of the part is reached. Then changing directions, the process continues back in the opposite direction, obtaining the Y-axis values along the opposite edge of the part.

Figure 7:
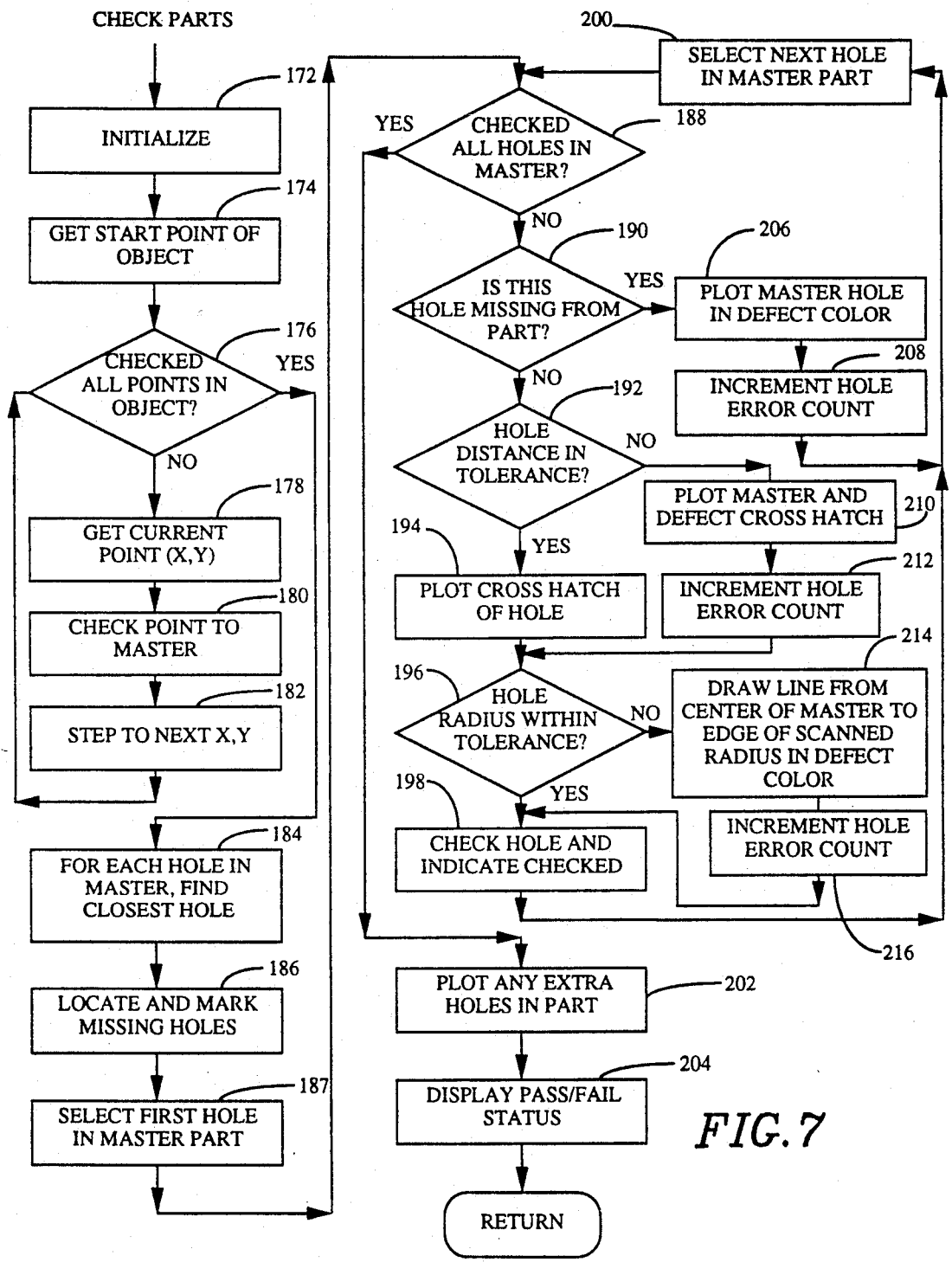
FIG. 7 is a flow chart of the part checking process of the present invention.

The "check parts" process is shown in FIG. 7 wherein after an initialization is performed (block 172) a starting point to be checked is selected (step 174); in the preferred embodiment, the starting point will be selected to be a point where the X-axis intersects the edge of the rotated part. Decision block 176 then determines whether all points in the object being checked have been compared with the master, and if not, the current point (X,Y) is obtained in step 178. That point is checked against the master in step 180, described in greater detail in connection with FIG. 9, and then the process steps to the next X, Y point in the object currently being checked (block 182).

The process loops back to decision block 176 to determine whether any points remain to be checked. If all points have been checked in the current object, the process then enters block 184 which finds, for each hole in the master part, the closest hole in the scanned part. Missing holes are located and marked in step 186. Now, step 187 is entered which selects a first hole in the master part for further processing. Decision block 188 is entered whereupon if all the holes in the master part have not been checked, then decision block 190 is entered to determine whether the current hole in the master is missing from the part being checked. If the hole is not missing then decision block 192 is entered wherein the hole distance of the part being checked is compared to see if it is within tolerance. If the center of the hole is within tolerance distance from the origin then step 194 is entered wherein a crosshatch is plotted on the graphics screen at the center of the current hole. Decision block 196 determines whether the radius of the current hole is within tolerance to the master and if so, step 198 is entered wherein the check hole function is performed as will be discussed in conjunction with FIG. 8, and the hole is then marked as having been checked. The process enters block 200 wherein the next hole in the master is selected and the process loops back to decision block 188 to determine whether all holes in the master have been checked. If at this point all holes in the master have been checked, the process jumps to step 202 wherein any extra holes in the scanned part are plotted and step 204 displays the pass/fail status of the current part to complete the "check parts" function. A part fails inspection if the failure count (discussed in conjunction with FIG. 9) exceeds a certain number (e.g. 3) or if there is an error in the holes in the part (e.g. extra holes, missing holes, hole off center or incorrect hole radius).

Referring back to decision block 190, if the master hole currently being checked is missing from the scanned part then step 206 plots the master hole on the display in a defect color (where the defect color is a color chosen to indicate that a defect has been located, e.g. red). The hole error count is incremented (step 208) and the process then continues with process step 200, the "select next hole in master" step.

Referring again to decision block 192, if the distance of the hole center from origin of the scanned part is not within tolerance, the system will perform block 210, plotting a crosshatch for the master hole center and plotting a defect color crosshatch for the scanned hole center, and incrementing the hole error count (step 212). The process will then continue with decision block 196.

Figure 22:
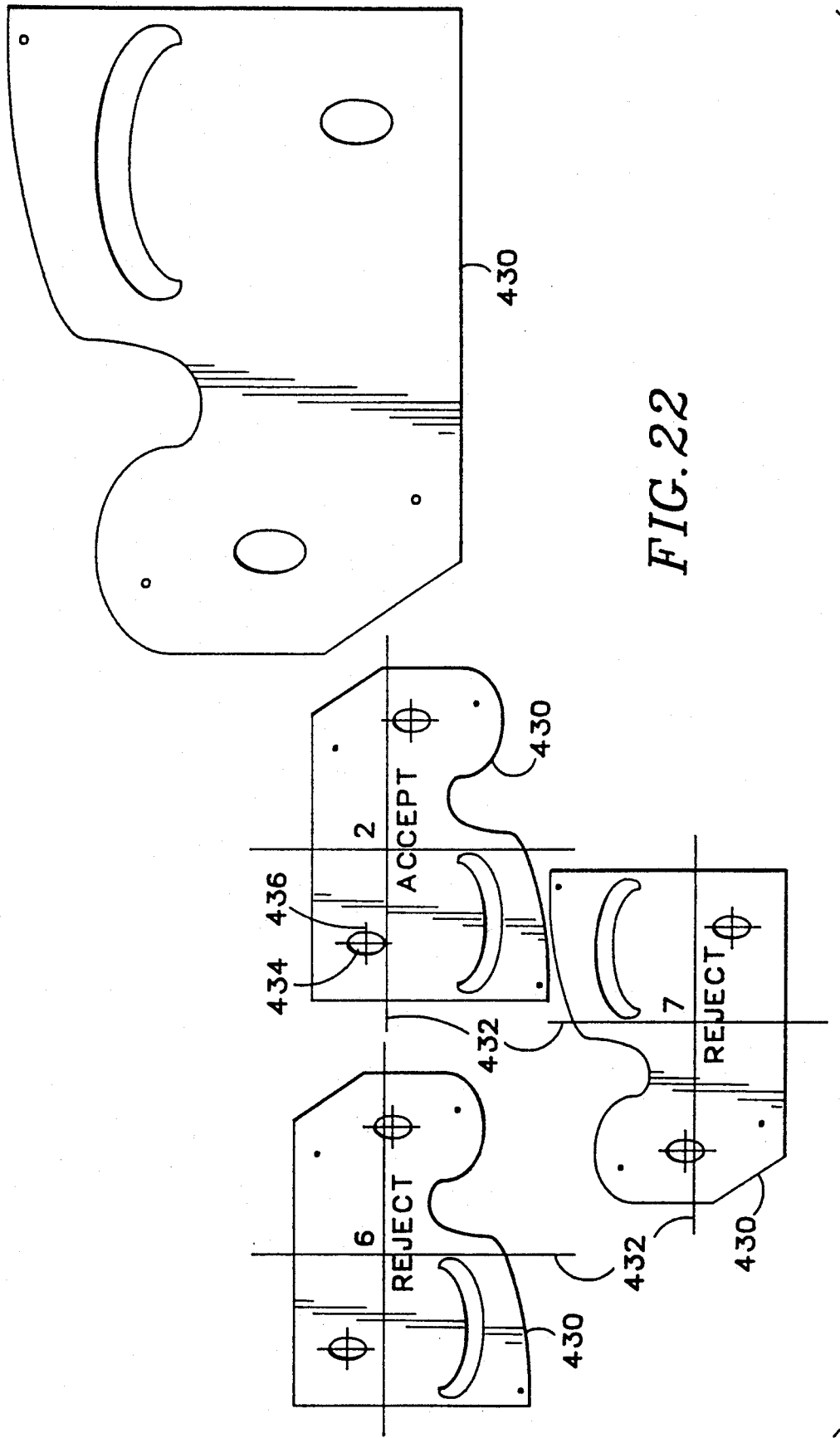
FIG. 22 is an example of a typical graphic display of a scanned part.

Referring to block 196, if the radius of the scanned hole is not within tolerance, then block 214 is performed wherein a line is drawn on the graphics display from the center of the master hole to the edge of the scanned hole radius, using the defect color. Step 216 next takes place wherein the hole error count is incremented and processing continues with step 198 as described above. FIG. 22 illustrates a typical graphic display produced at the end of the check function of FIG. 7. The currently scanned part 430 is displayed on the right half of a graphic display screen while other parts on the scan table are displayed on the left half of the graphic display. The left half of the graphic display will plot the centroid of each part via intersecting lines 432, the part number is displayed near the centroid (in this illustration, parts 2,6 and 7 are shown) and each hole 434 is plotted with a cross hatch 436 indicating the center of the hole. The pass/fail status of the part is displayed near the centroid, and in this case part 2 shows an accepted status, while parts 6 and 7 show a reject status. Note that the scanned part on the right half of the screen is displayed in a rotated form, oriented to the X-axis, while the parts on the left half of the screen are displayed in the orientation as scanned from the table 54; the parts are graphically represented as an outline of each part with the orientation and centroid plotted.

Figure 8:
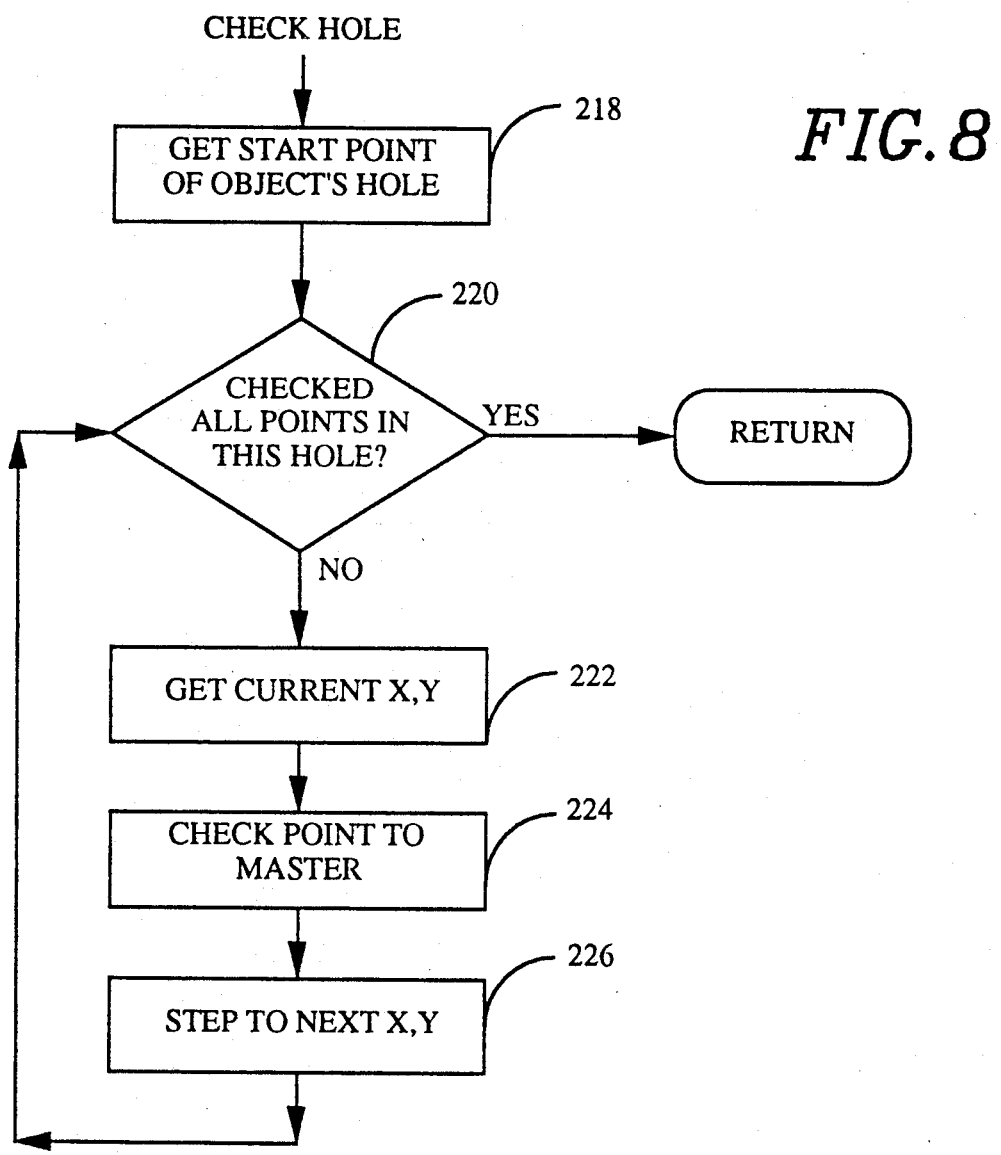
FIG. 8 is a flow chart of the hole checking function of FIG. 7.

Referring now to FIG. 8, the "check hole" process of block 198 of FIG. 7 is described in further detail. The start point of the current hole is selected (block 218) and decision block 220 determines whether all points in this hole have been checked. If not, the current X, Y point is obtained (block 222) and the point is checked against the master (block 224). Block 224 is the same process performed in block 180 of FIG. 7 and is described in conjunction with FIG. 9 herein. The process then steps to the next X, Y point in the current hole (block 226) and the process loops back to decision block 220. If in block 220 all points in the current hole have been checked, then the "check hole" process is completed.

FIG. 9 illustrates the "check point to master" process steps of block 180 (FIG. 7) and block 224 (FIG. 8) wherein the point being checked is rotated and translated (block 228) in accordance with the following formulas:

the rotated point X'Y' is produced by $$X' = X(\cos(\theta)) - Y(\sin(\theta)) + \text{XOFFSET, and}$$

$$Y' = X(\sin(\theta)) + Y(\cos(\theta)) + \text{YOFFSET}$$

where "theta" is a rotation angle and "XOFFSET" and "YOFFSET" are translation coefficients for plotting on the graphics screen. Step 230 finds the point (XM, YM) in the master part with a minimum distance to the point (X, Y) in the part being checked. Note, however, that not every point in the master part is checked for minimum distance; only a small number of points beyond the current master point will be compared. In the preferred embodiment of the present invention, between four and two hundred points are checked to find a minimum. In decision block 232, if the minimum distance from block 230 is within tolerance, then the object point (X', Y') is plotted on the graphics screen (step 234), the maximum error distance is updated if necessary (step 236) and the process is completed.

Referring again decision block 232, if the minimum distance is not within tolerance then the master point is rotated and translated to produce XM' and YM' wherein $$XM' = XM(\cos(\theta)) - YM(\sin(\theta)) + \text{XOFFSET}$$
and $$YM' = XM(\sin(\theta)) + YM(\cos(\theta)) + \text{YOFFSET}$$

(step 238). The rotated and translated master point (XM', YM') is then plotted (block 240) on the graphics display in a color indicating that it is a master point (e.g. blue). The rotated and translated object point (X',Y') is also plotted in a defect color (block 242) thus providing an indication of the expected and actually scanned points. A failure counter is incremented in block 244 and the process continues execution with block 236 wherein the maximum error distance is updated and the process is completed.

Figure 10:
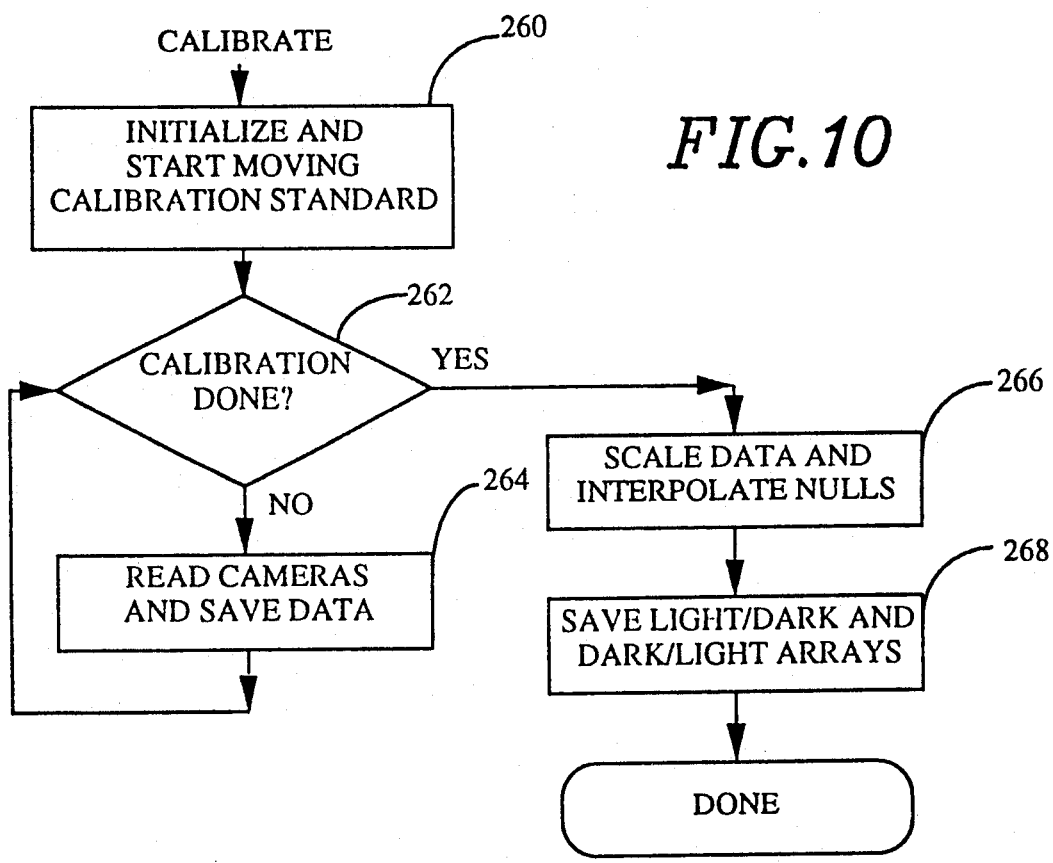
FIG. 10 is a flow chart of the calibration procedure for the present invention.

Referring now to FIG. 10, the method of calibrating the visual inspection system will be described. Calibration is accomplished through the use of a Sony magnascale and a calibration standard of known thickness, wherein the calibration standard is scanned across the field of view of the cameras while the position of the standard is read from the magnascale. Once gathered, the calibration information is stored for use during the scanning procedure. Since part thickness will affect the image presented to the cameras, a separate calibration for parallax error should be performed for the various thicknesses which will be scanned during system operation. The calibrations are stored according to part thickness and thus may be retrieved at scan time based on the part thickness being scanned. Therefore, system calibration need only be performed once using the multiple thicknesses to be encountered. It will be necessary to recalibrate the system when adding new part thicknesses to the repertoire of parts to scan.

Figure 11:
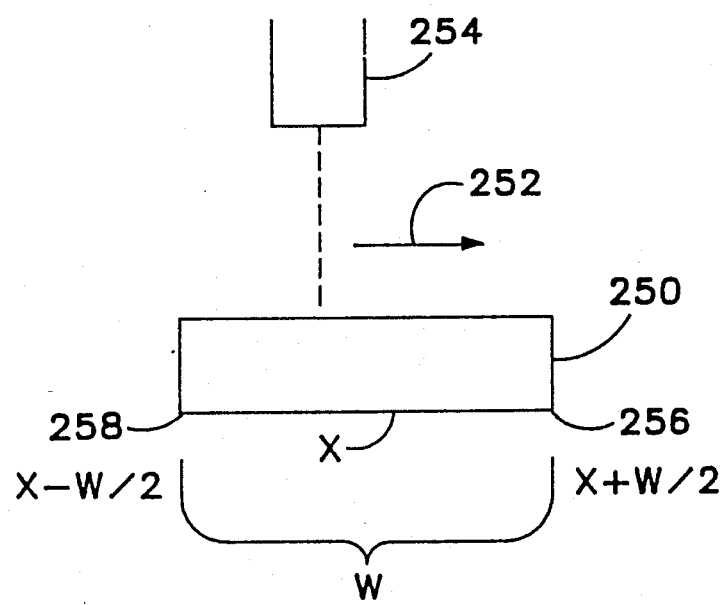
FIG. 11 is a view illustrating the calibration process.

Referring to FIG. 11, the calibration standard 250 has width W and is scanned in the direction indicated by arrow 252. The camera 254 sees a dark-to-light transition at point 256 which has a coordinate value of X+W/2, where X is the position value reported by the magnascale (i.e. the center of standard 250). Camera 254 also sees a light-to-dark transition at position 258 which has the coordinate value of X−W/2. The thickness of calibration standard 250 is variable and is entered into the calibration system from an operator's console when beginning the calibration process.

Referring again to FIG. 10, the calibration process comprises the steps of initializing the system and setting the calibration standard in motion (step 260), determining whether the calibration procedure is finished (decision block 262) and if calibration is not completed, reading the camera data and saving both light-to-dark and dark-to-light transition information in an array value corresponding to the position of the calibration standard. The process continues to loop through decision block 262 and process block 264 until the calibration scan is complete whereupon the process will enter block 266 which will scale the data, and interpolate for erroneous data values to provide compensation if, for example, a dust particle on the scanning surface generates erroneous data. Process step 268 is then performed whereupon the calibration data for both cameras is saved for use during scanning. The light-to-dark and dark-to-light transitions encountered during calibration are stored in separate arrays. This then completes the calibration process.

According to the present invention the master part to be used for comparison may be either a scanned part which is generated from the data from the scanning table, or the master part may be derived from a digital representation of the part such as computer aided design information which describes the part. The preferred embodiment of the present invention includes software capable of taking data in an IGES data format and using such data as the master part. Such a system is advantageous in that the design data used to control machinery which fabricates a part is the same data employed in testing the fabricated part for manufacturing errors. The routine for extracting master part data from an IGES format file is discussed in conjunction with FIGS. 12, 18–21 and 24–26 herein and corresponds to the process used for scanning a part from the scan table as described above in conjunction with FIG. 6A.

Figure 23:
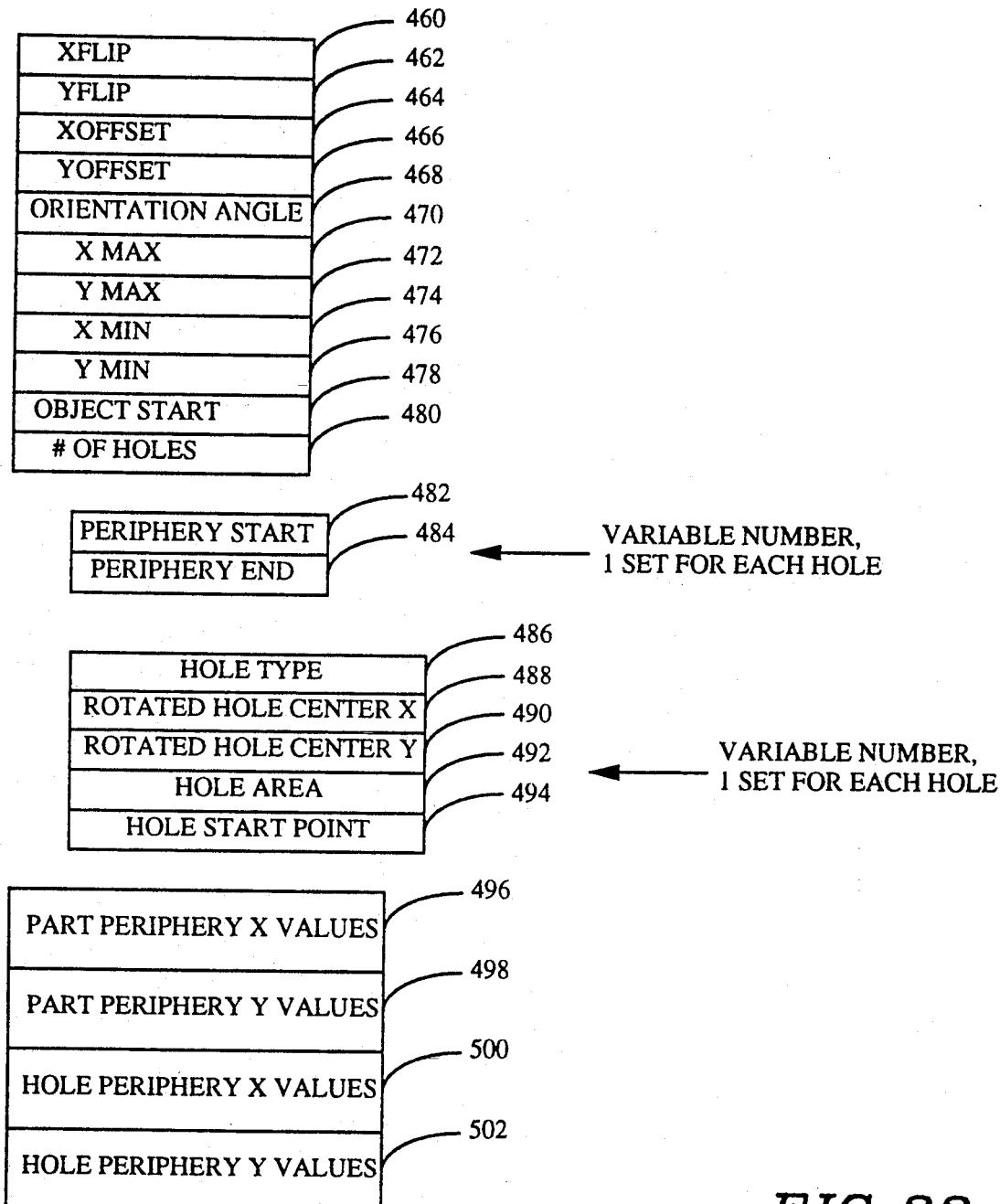
FIG. 23 illustrates the data storage format of master part information.

Referring to FIG. 23, the information generated and stored for scanned parts and master parts is considered. The master part library can consist of multiple entries in the format described herein, with one entry generated for each unique master part. XFLIP 460 is an indicator of which way the X-axis is oriented; if XFLIP is negative, positive X values are to the left of the part centroid. Conversely, if XFLIP is positive, positive X values are to the right of the centroid. YFLIP 462 is similar to XFLIP and indicates whether positive Y-axis values are above or below the part centroid. XOFFSET 464 is the maximum X-axis value of the part plus the X-axis value of the centroid of the part, while YOFFSET 466 is the minimum Y-axis value of the part minus the Y-axis value of the part centroid. The part orientation angle is stored in ORIENTATION ANGLE 468, and is used in rotating the parts. X MAX 470, Y MAX 472, X MIN 474 and Y MIN 476 contain the maximum and minimum X-axis and Y-axis values of the part. X MAX is the most positive X measured from a line normal to the axis of least inertia of the part, Y MAX is the most positive Y value measured from the axis of least inertia, X MIN is the most negative X measured from a line normal to the axis of least inertia of the part while Y MIN is the most negative Y value measured from the axis of least inertia. OBJECT START 478 indicates the point on the part at which comparison should begin when comparing the master part with a scanned part.

The next item, NUMBER OF HOLES 480, indicates how many holes the current part contains, and immediately following are PERIPHERY START 482 and PERIPHERY END 484 which indicate the start and end in the periphery storage area for each hole. The number of entries 482 and 484 are variable, depending upon the number of holes in the part; one pair of PERIPHERY START and PERIPHERY END values will be present for each hole in the part. Following the periphery values is a set of five values: HOLE TYPE 486, ROTATED HOLE CENTER X 488, ROTATED HOLE CENTER Y 490, HOLE AREA 492 and HOLE START POINT 494. These values represent the type of hole, the X-axis and Y-axis values of the center of the hole after rotation, the area of the hole and the starting point of the hole (used to determine where to begin comparison between master and scanned part holes). There will be a variable number of sets of these values, one for each hole in the part. Immediately following the hole information is the PART PERIPHERY X VALUES 496 and PART PERIPHERY Y VALUES 498 which are arrays of X-axis and Y-axis values containing the part periphery information as calculated by the periphery routine. The final items are the HOLE PERIPHERY X VALUES 500 and HOLE PERIPHERY Y VALUES 502 which contain the arrays of hole periphery information.

Once a part has been scanned from the scanning table, and it is desired to check the scanned part against a master part, the appropriate master part is located and retrieved from the master part library. If the specific part number being scanned is known, the master may be retrieved via the master part number, for example, by entering the master part number at an operator console. However, when a multiple number of distinct parts are being checked, the appropriate master for each individual part type will have to be located and read in for comparison. Therefore, a method of matching a scanned part with the appropriate master part has been devised wherein a part identification is developed which consists of the area of the object, the maximum Y length of the part, the maximum X length of the part, the average X value of the part, the average Y value of the part, the sum of the X values of the centers of all holes in the part divided by the number of holes and the sum of the Y values of the centers of all holes in the part divided by the number of holes. The part library is then scanned and these factors from the scanned part are compared with the corresponding factors from the master parts in the library until an appropriate match is found.

The preferred embodiment of the present invention uses the absolute value of the difference between these various factors times a weighting factor, each of the individual terms is summed into a weighted sum, and the master part with the closest match (i.e. the lowest weighted sum) is selected. In one embodiment of the invention the various factors were given the following weights: object area, weight 2; Y maximum length, weight 3; X maximum length, weight 3; average X value, weight 2; average Y value, weight 2; hole X centers, weight 0.08; and hole Y centers, weight 0.08. It can therefore be appreciated that extra holes or a lack of holes in a scanned part will not significantly disrupt the part location method.

Figure 13:
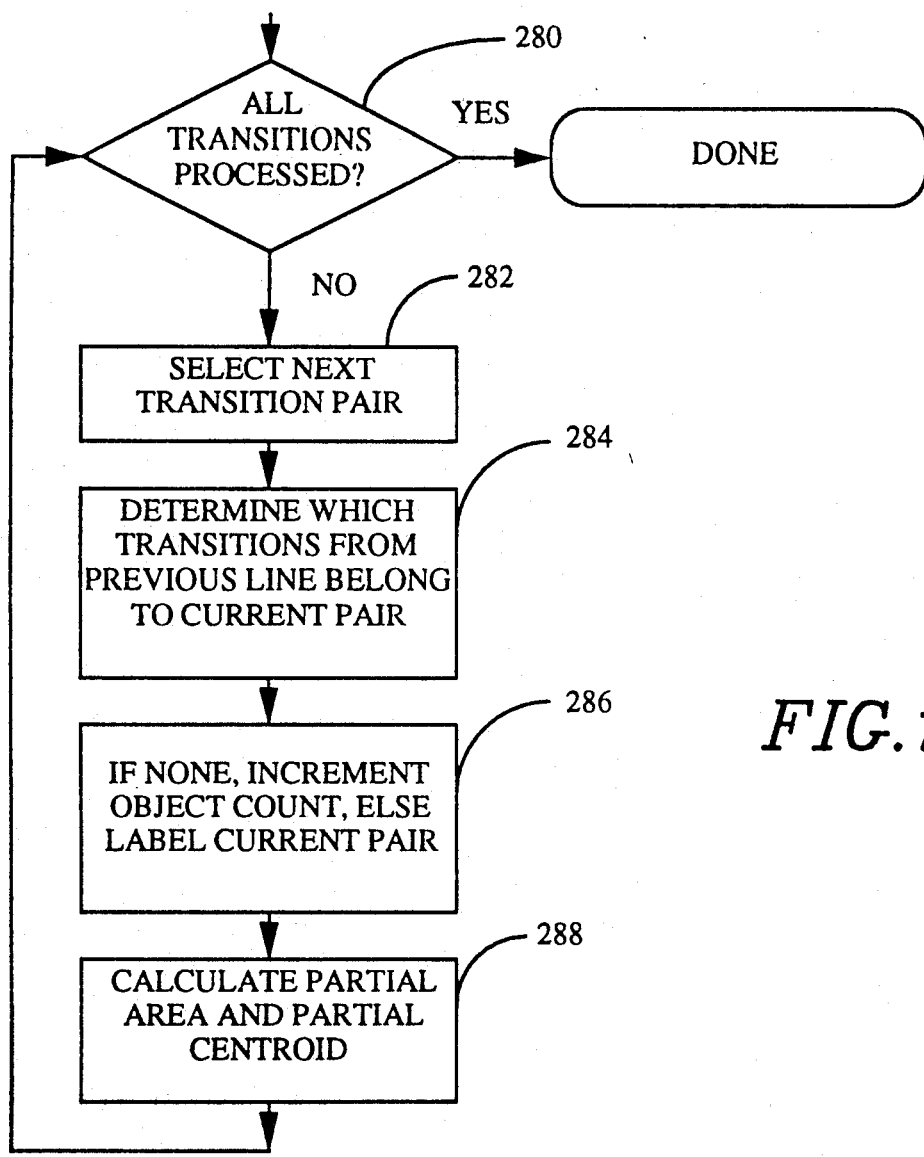
FIG. 13 is a more detailed flow chart showing the steps for finding objects of FIG. 6A.
Figure 14:
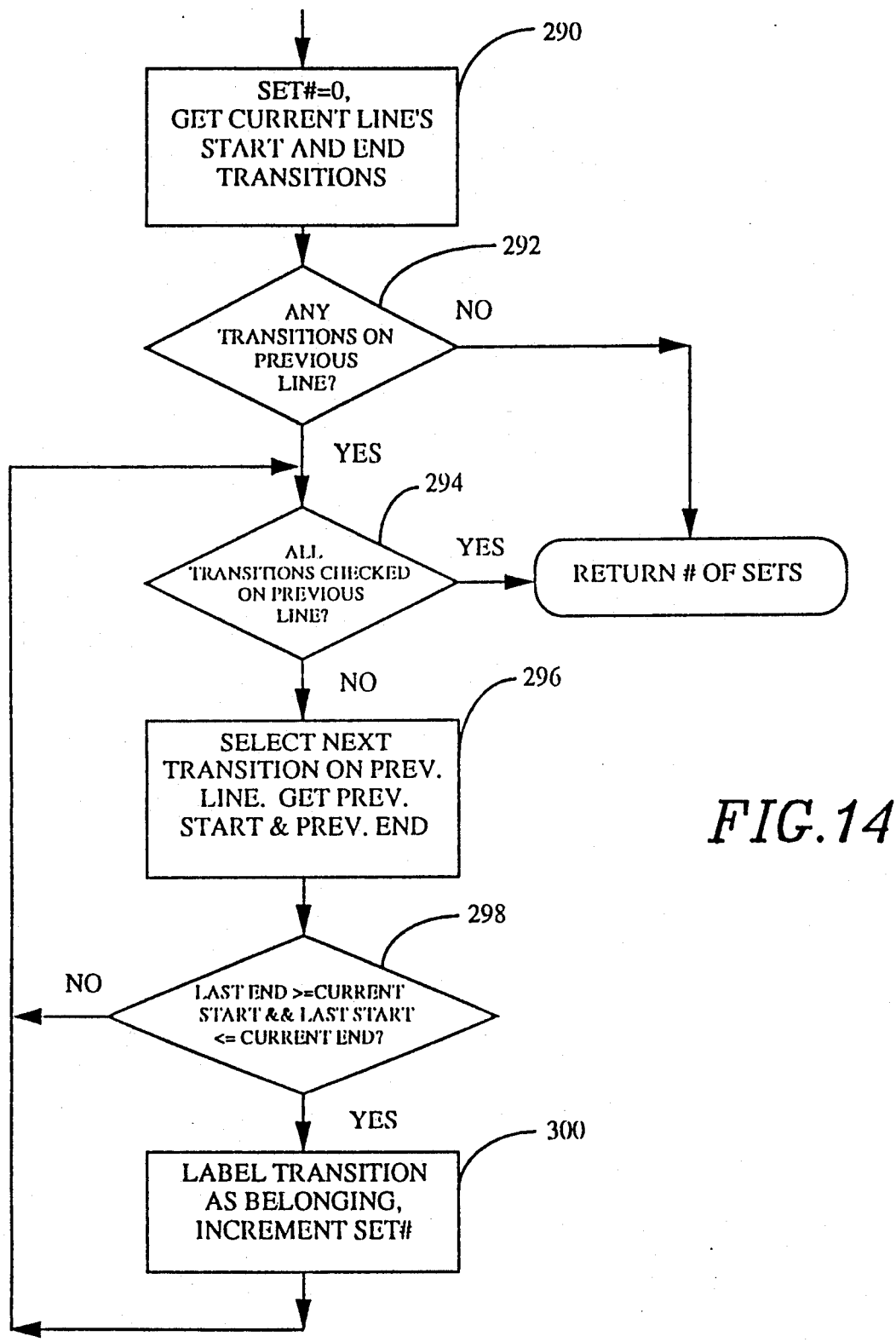
FIG. 14 is a more detailed flow chart of the steps for selecting objects from previous scan lines and matching them with objects in current scan lines.

Referring now to FIGS. 13 and 14, the "find objects" block 164 of FIG. 6A will be discussed in greater detail. Since any given object will have at least a pair of transitions (a light-to-dark and dark-to-light transition) all transitions are processed in pairs. Thus, an object has a solid portion between transitions while a hole would have light and light-to-dark transition). While FIGS. 13 and 14 show the "find objects" procedure, the "find holes" procedure is very similar. In finding an object, the processor first determines whether all transitions in the current line have been processed (decision block 280) and if not, the next transition pair is selected (block 282) and the process then determines which transitions from a previous transition line belong to the current pair or transitions (block 284), as will be discussed in greater detail with reference to FIG. 14. If no transitions from the previous line belong to the current pair then a new object has been located, and the count of objects is incremented. If any transitions from the previous line do belong to the current pair, the object is labeled (block 286).

Next, the partial area, partial X centroid value, and the partial Y centroid value are calculated and summed (block 288) for use in determining the total part area and centroid X and Y values when the scan is completed. The process then loops back to decision block 280 wherein, if all transition pairs have been processed, the routine is completed.

Referring now to FIG. 14, the routine for determining which transitions from the previous line belong to the previous pair is described in greater detail. The processor initially sets the number of sets located to zero and obtains the current start and end transition points for the current line (block 290). Decision block 292 determines whether there are any transition on the previous line. If none, then the routine exits, returning zero. If, however, there were transitions on the previous line, decision block 294 determines whether all of the transitions of the previous line have been checked yet. If so, then the process is complete and returns number of sets, but if not, block 296 is entered wherein the next start and end transition from the previous line are selected. According to decision block 298 the previous ending transition is compared with the current starting transition and the previous starting transition is compared with the current ending transition to determine whether this transition belongs with the current transition pair in the current line (block 298). If the previous transition pair does not belong with the current transition pair, then the process loops back to decision block 294 to determine whether all of the previous transitions have been tested. If however, the previous transitions being tested do belong with the current transition pair, then the processor indicates that a transition pair set has been found and the transition is labeled as belonging with the previous transitions so located (block 300). The process then loops back to continue execution with decision block 294 to determine whether all transitions on the previous line have been checked. When this process is complete, the processor continues execution with block 286 of FIG. 13.

Figure 15:
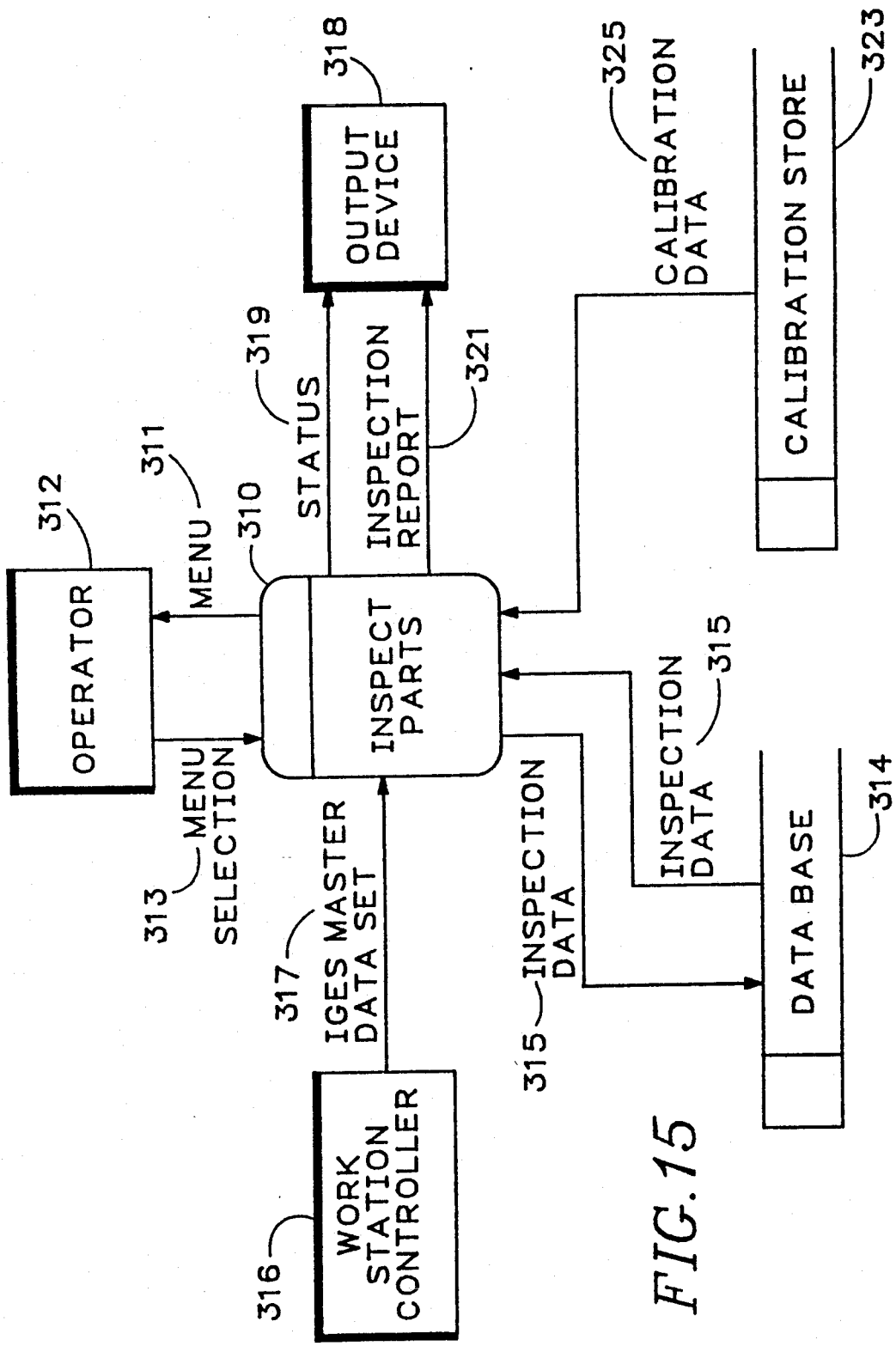
FIG. 15 is a data flow diagram of the overall system operation of the present invention.

FIG. 15 is a data flow diagram of the overall system of the present invention. In operation, the sheet metal vision inspection system 310 presents a menu 311 to an operator 312 whereupon the operator makes a menu selection 313 which is returned to the inspection system. The system sends inspection data 315 to a data base 314 which contains the master and inspection data. The data base also provides inspection data back to the sheet metal inspection system and calibration store 323 provides calibration data 325 to system 310. Work station controller 316 provides Initial Graphics Exchange Standard (IGES) master data information 317 to the system 310. Work station controller 316 can be, for example, a computer aided design system upon which the part being inspected was designed. The output device 318 receives status 319 and inspection report 321 from the inspection system and can comprise for example, a graphic display, a text display, a printer display or a form of mass storage.

Figure 16:
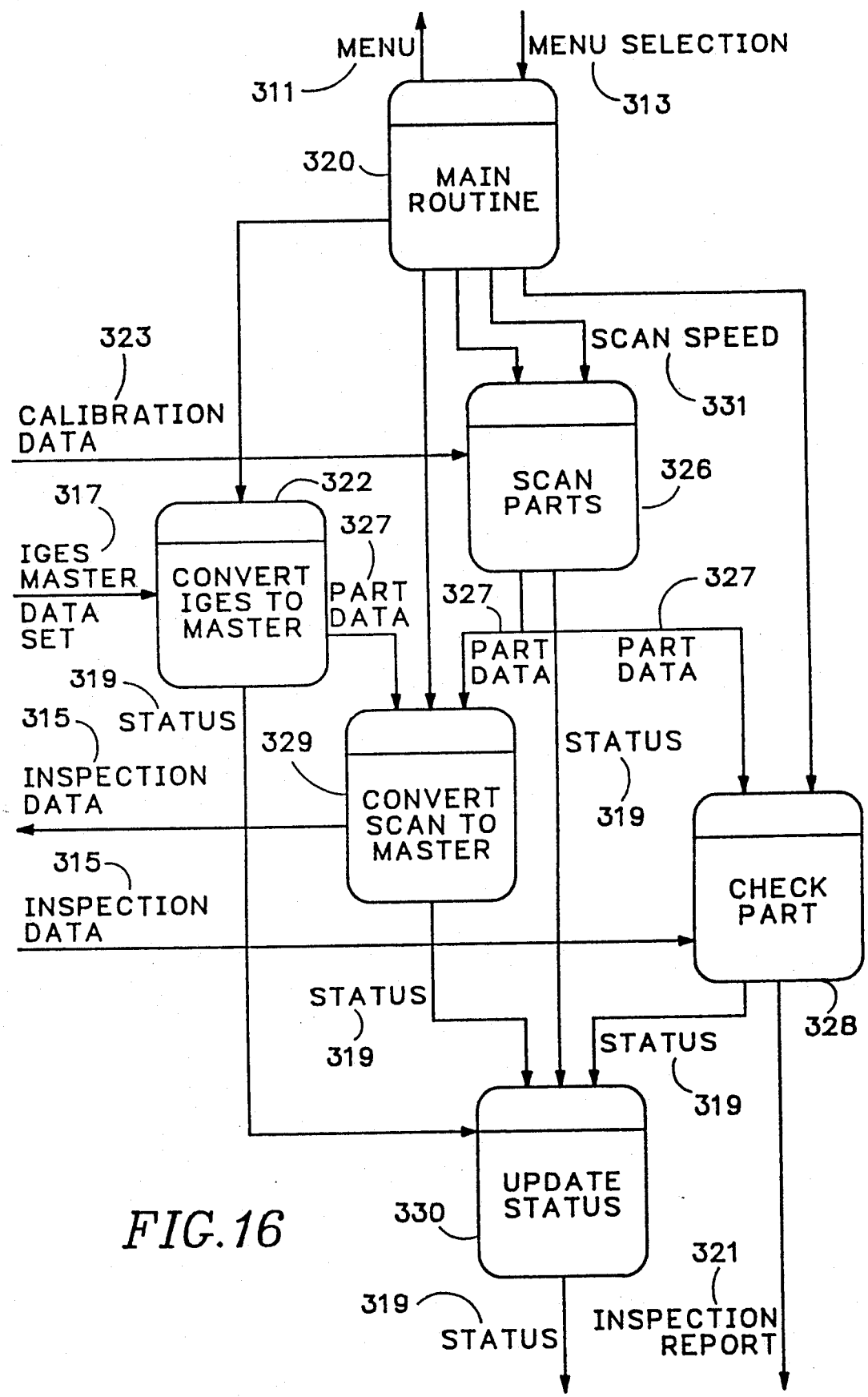
FIG. 16 is a more detailed data flow diagram of the inspection function of FIG. 15.

Referring now to FIG. 16, when a menu selection is received by main routine 320 an appropriate module is executed. If a command to convert an IGES format file to the master data format is received, then process 322 is invoked and receives IGES master data 317, and provides part data 327 to process 329 which converts the data to the master data. The "convert scan to master" process 329 generates inspection data 315 which may be stored in mass storage. If the menu selection is such as to enter the "scan part" process 326, the system reads calibration data 323, scan speed data 331 and generates part data 327 which may be provided to other modules. The "check part" process 328 will take the part data 327 generated by process 326 and compare it with inspection data 315 and generate inspection report data output 321. Modules 322, 324, 326 and 328 all generate status data 319 which is provided to "update status" process 330 which generates status output 319.

Figure 17:
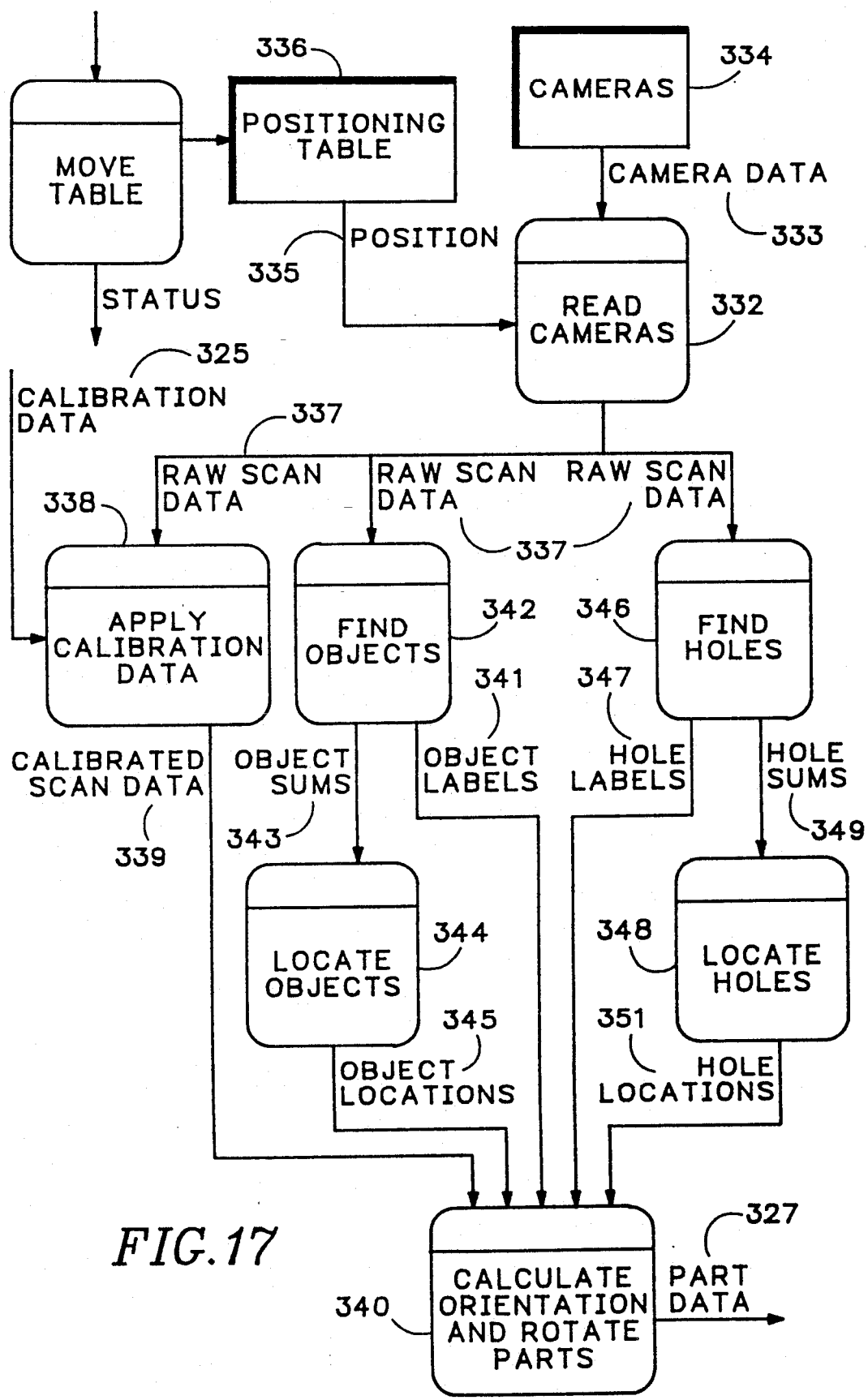
FIG. 17 is a more detailed data flow diagram of the "scan parts" process of FIG. 16.

FIG. 17 is a data flow diagram corresponding to the scan portion of the flow chart of FIG. 5. Block 332 will read camera data 333 from cameras 334 and position data 335 from positioning table 336. The raw scan data 337 thereby generated by block 332 is applied to three different process blocks. First, the raw scan data 337 is provided to the "apply calibration data" block 338 which will read calibration data 325 and produce calibrated scan data 339 as output fed to "calculate orientation and rotates parts" block 340. Second, the raw scan data from block 332 is supplied to the "find objects" block 342 which feeds object label data 341 to block 340 and object sum data 343 to "locate objects" block 344, whereupon "locate objects" block 344 provides object location data 345 to block 340. Third, the "find holes" process block 346 receives the raw scan data from block 332 and generates hole labels 347 provided to block 340 and hole sum data 349 provided to the "locate holes" process block 348 whereupon block 348 generates hole location data 351 fed to block 340. Having received all the data inputs described above the "calculate orientation and rotate parts" block 340 will generate part data 327 as output. Block 340 corresponds to the "orient parts" and "rotate parts" blocks 130 and 132 discussed in conjunction with FIG. 5.

Figure 12:
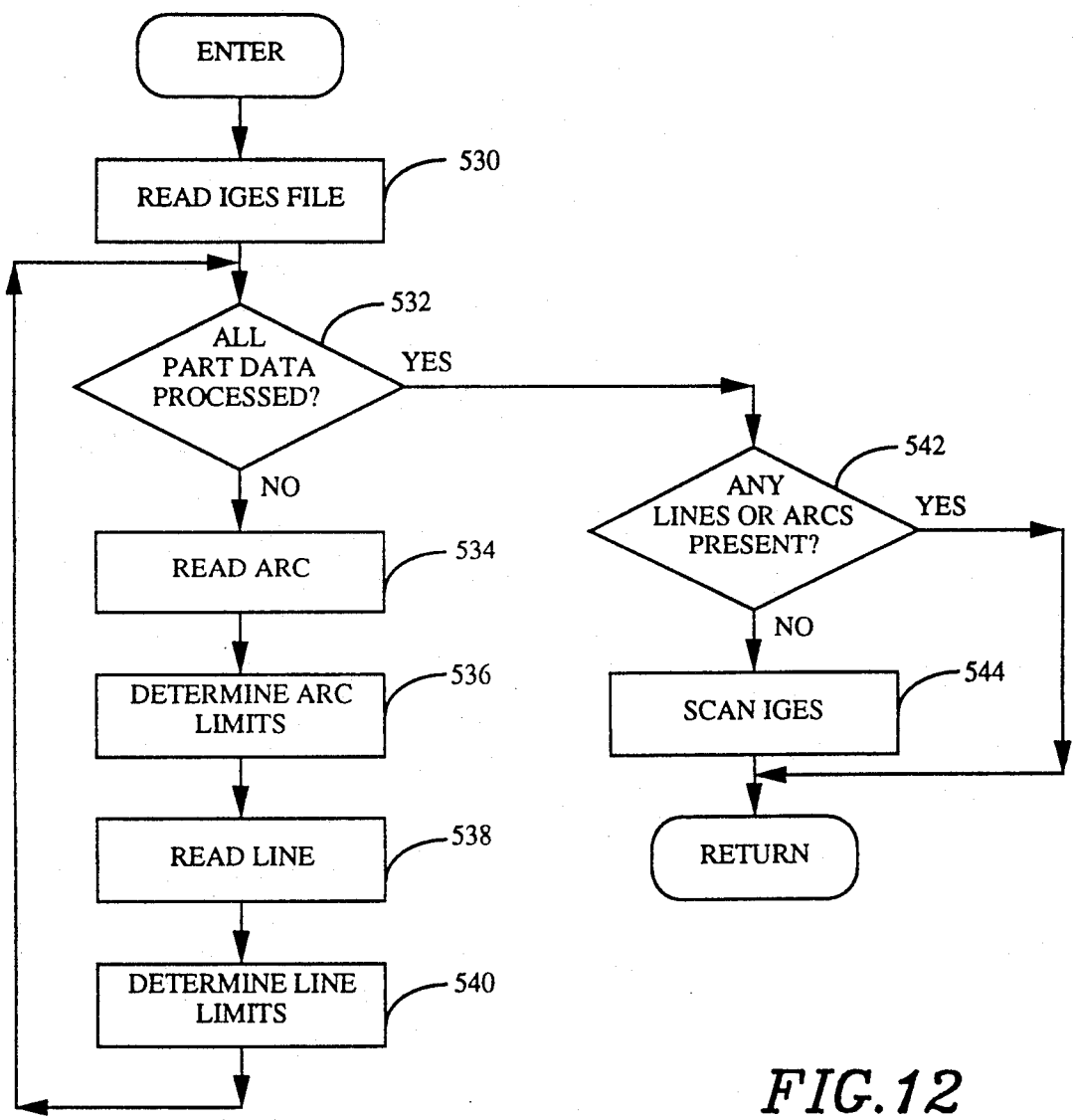
FIG. 12 is a flow chart of the process of extracting master template data from a standard graphics format data file.

The conversion of IGES format data into master part data will be better understood with reference to FIGS. 12, 18-21 and 24-26. The IGES format file will contain information for a part, defining the part as a collection of arcs and lines. In order to use the information, the present invention converts the IGES format information into scan information as will be described. Referring to FIG. 12, the process begins by reading in the information contained within an IGES format data file (block 530). Decision block 532 tests whether all the part data from the file has been processed and if not, an arc is read from the data file (block 534). The arc information read from the file produces an arc defined by the X,Y values of its start point (XS,YS), center point (XC,YC) and end point (XE,YE). The process then determines the arc limits (block 536) setting the maximum and minimum X,Y values for the arc. Next, a line is read from the IGES data file (step 538) and the line limits (step 540) are determined for setting the maximum and minimum X,Y values for the line read, each line being defined by its start and end points. The routine will then proceed with decision block 532, continuing to process the data file until all part data has been taken care of. Once decision block 532 determines that all data has been processed, decision block 542 is then entered to determine if any lines or arcs were present in the data file, and if not, the program is done. However, if there were lines or arcs present, the program continues with the SCAN IGES block 544 for performing the scanning operation.

Figure 24:
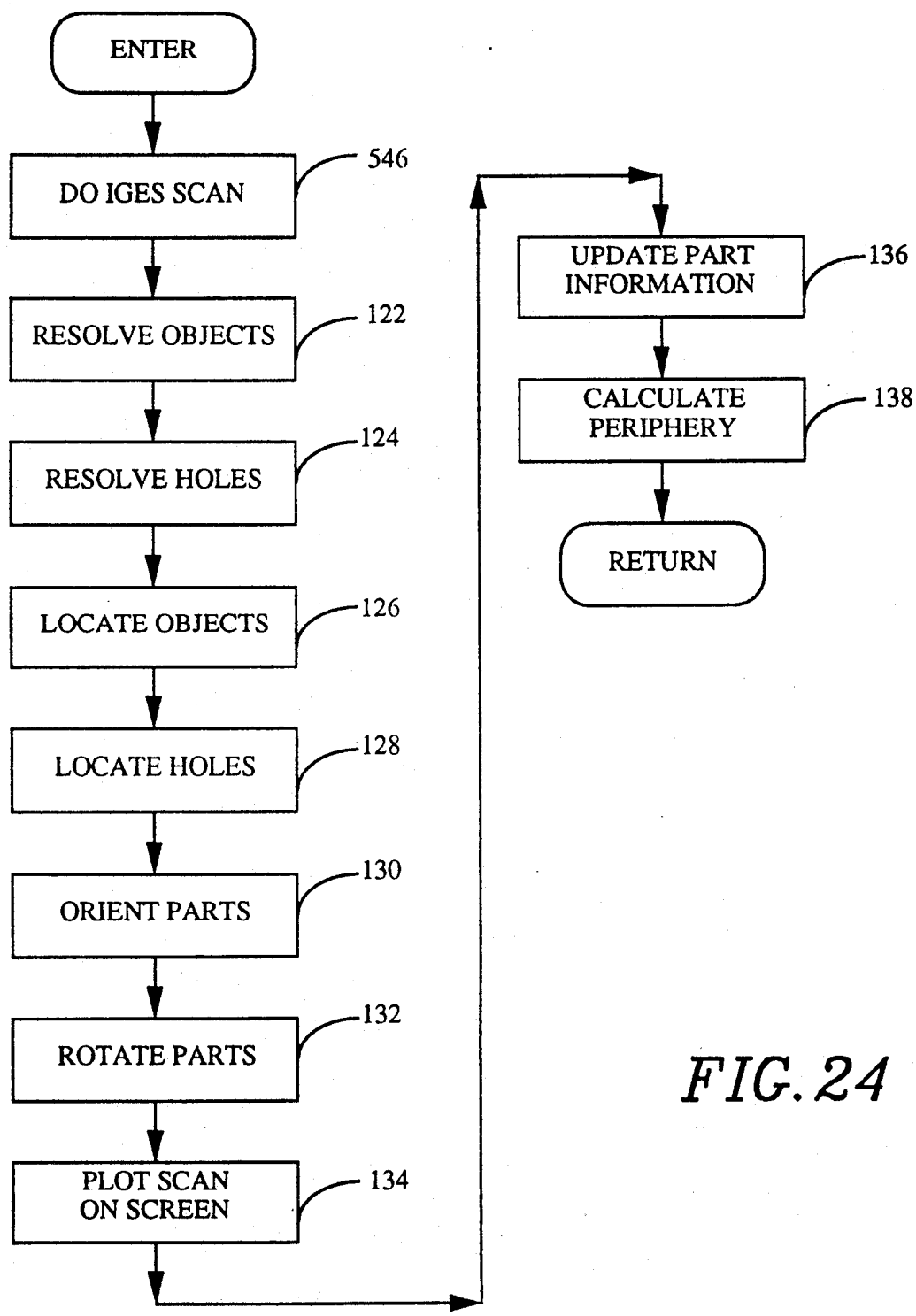
FIG. 24 is a more detailed flowchart of the "scan IGES" process of FIG. 12.

Referring now to FIG. 24, the SCAN IGES block 544 of FIG. 12 is described in greater detail. The routine begins by performing the DO IGES SCAN block 546, wherein the information extracted from the IGES file is converted into run length encoded data corresponding to the data which would have been generated by scanning an actual part on the scan table as described herein with reference to FIG. 5. The program then continues as if a part had actually been scanned via the cameras and the scan table. During conversion, located objects and holes are assigned labels and may be labeled more than once. Therefore, when the conversion is completed, the objects picked up by the conversion are resolved (step 122) wherein the object labels are reduced to the smallest common label; similarly in step 124, the holes within objects from the conversion are resolved wherein the hole labels are reduced to the smallest common label. The resolve processes insure that a single label is assigned to each distinct object or hole. Next "locate objects" 126 is performed wherein the centroid of each object from the conversion is calculated using the method described hereinabove. Similarly step 128 locates holes wherein the centroids of the holes of any object from the conversion are calculated. Next, step 130 calculates the angle of orientation of each part, the parts located by the conversion are then rotated in the "rotate parts" step 132, and the parts as currently determined in the conversion are plotted on the screen (step 134). The part information is updated (step 136), wherein information about each of the parts located during the conversion is computed and tallied. The program then calculates the periphery of the located parts (step 138) wherein the periphery of the part is linked in a manner corresponding to connecting dots so that the part may be accessed via its periphery rather than via scan line information. This step is described in conjunction with FIG. 6B. After performing step 138, the scan and plot operation is complete.

Figure 25:
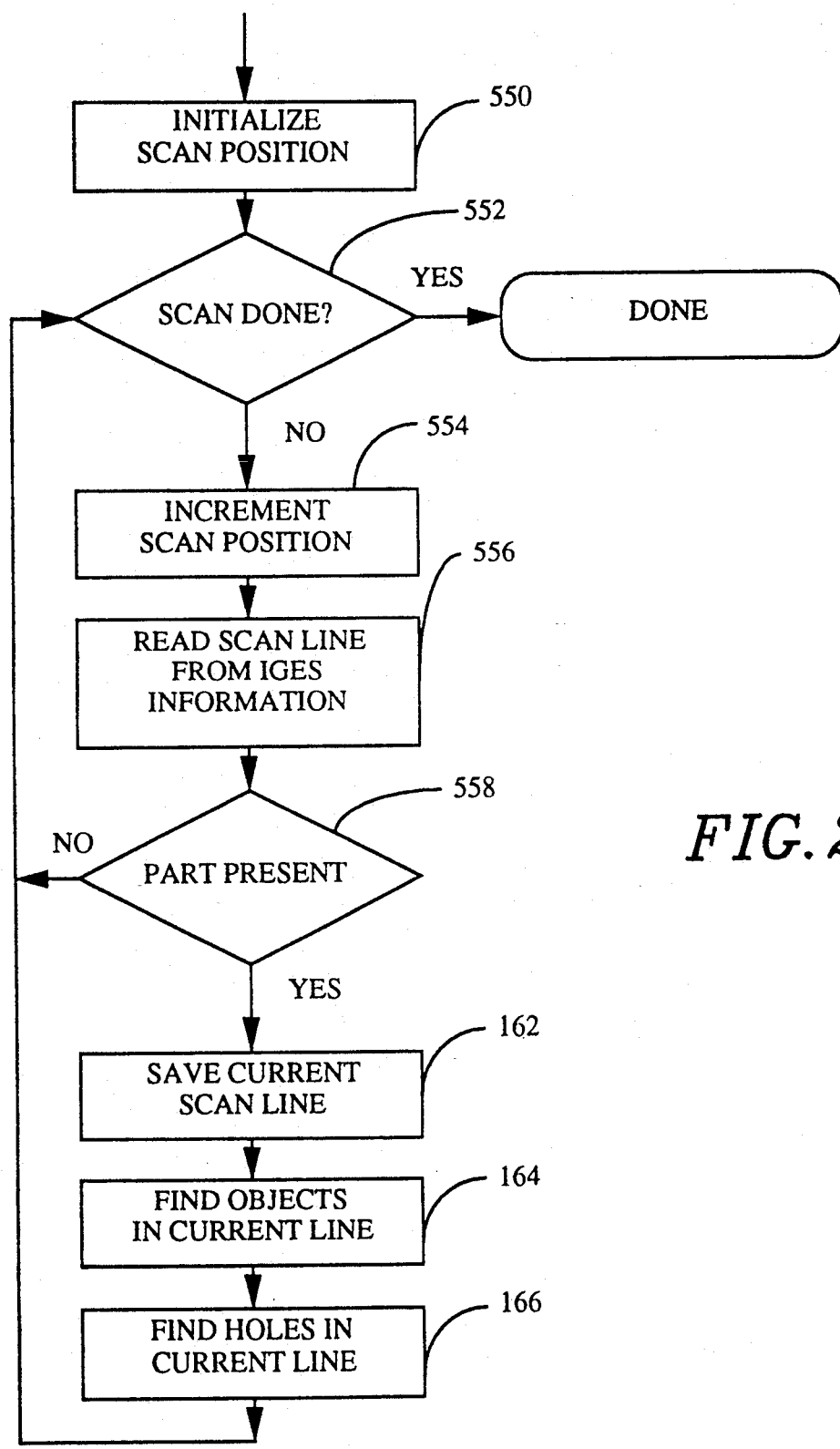
FIG. 25 is a more detailed flowchart of the "DO IGES SCAN" process of FIG. 24.

FIG. 25 describes the "DO IGES SCAN" block 546 of FIG. 24 in greater detail. The routine begins by initializing the scan position (block 550) wherein a value which simulates the position of the x-axis table 54 is generated. Decision block 552 tests whether the process is done (i.e. whether all possible scan positions have been generated). If not, block 554 is entered whereupon the scan position is incremented and block 556 reads a scan line from the IGES information extracted earlier, block 556 being described in conjunction with FIG. 26. Once the scan information is read, decision block 558 determines whether a part is present at the current scan position, and if not, the program loops back to continue execution with decision block 552. However, if a part was present, the current scan line is saved (block 162), the objects in the current line are found (block 164) and the holes in the current line are found (block 166). Blocks 162, 164, and 166 are the same processes and perform the same functions as described in conjunction with FIG. 6A. The program continues by looping back to decision block 552 to determine if the scan process is complete, and if complete, the process exits, but if not, execution continues with block 554 as described hereinabove.

Figure 26:
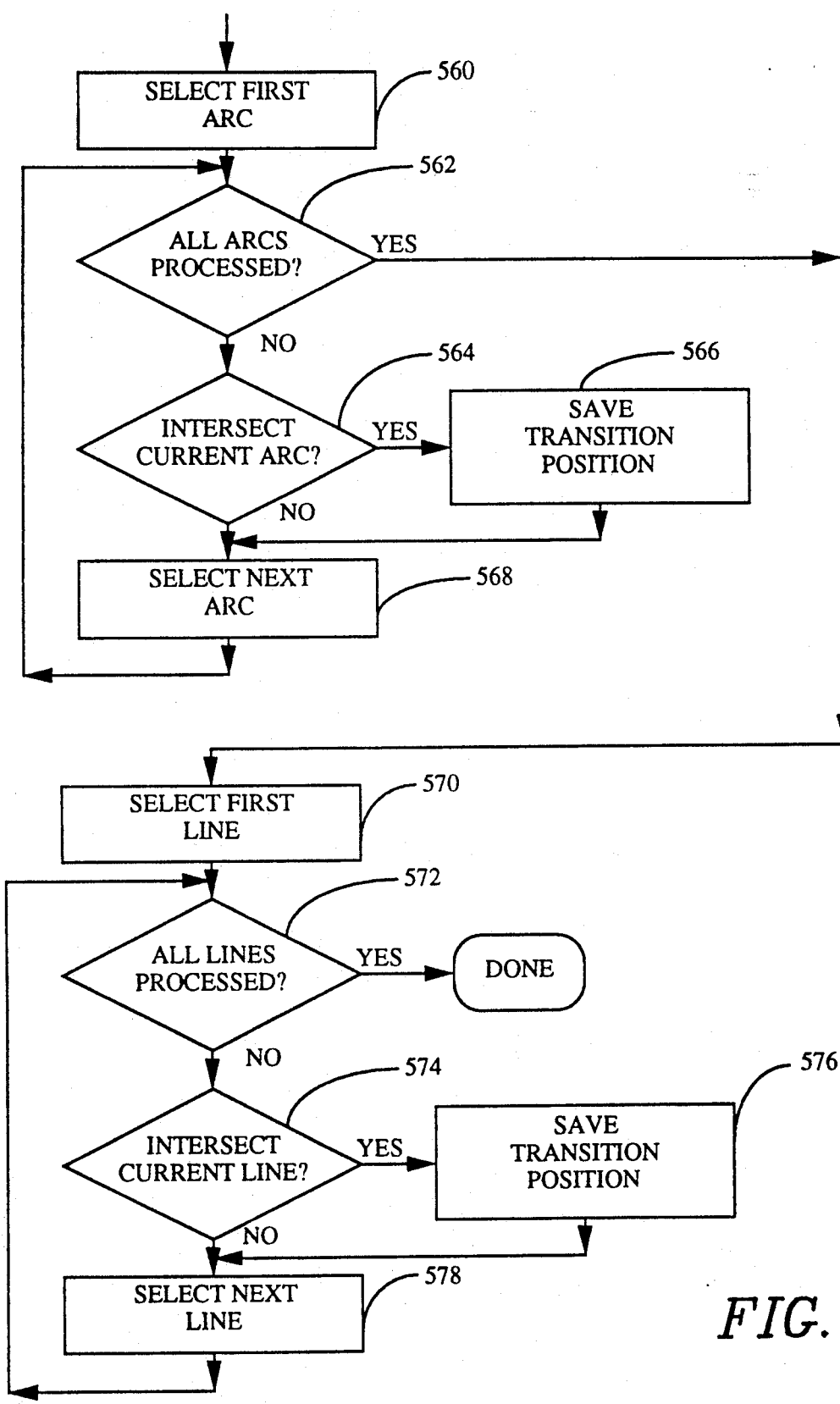
FIG. 26 is a more detailed flowchart of the "READ SCANLINE" process of FIG. 25.

FIG. 26 illustrates the steps of the read scan line from IGES information block 556 of FIG. 25 in further detail. Initially, a first arc is selected (step 560) from the IGES information and decision block 562 determines whether all arcs have been accounted for. If not, decision block 564 is entered whereupon it is determined whether the current scan position intersects the currently selected arc. If so, the transition information is saved (block 566) and block 568 is entered wherein a next arc is selected. If the current scan position did not intersect the current arc, block 566 is bypassed, and the program continues with block 568. Once block 568 is completed, the program loops back to continue execution with decision block 562, to determine whether all arcs have been taken care of. If all arcs have been processed, block 570 is entered wherein a first line is selected from the IGES information and decision block 572 determines whether all lines have been accounted for. If not, decision block 574 is entered whereupon it is determined whether the current scan position intersects the currently selected line. If so, the transition information is saved (block 576) and block 578 is entered wherein a next line is selected. If the current scan position did not intersect the current line, block 576 is bypassed, and the routine continues with block 578. Once block 578 is completed, the program loops back to continue execution with decision block 572, to determine whether all arcs have been input. If so, the process is complete.

Figure 18:
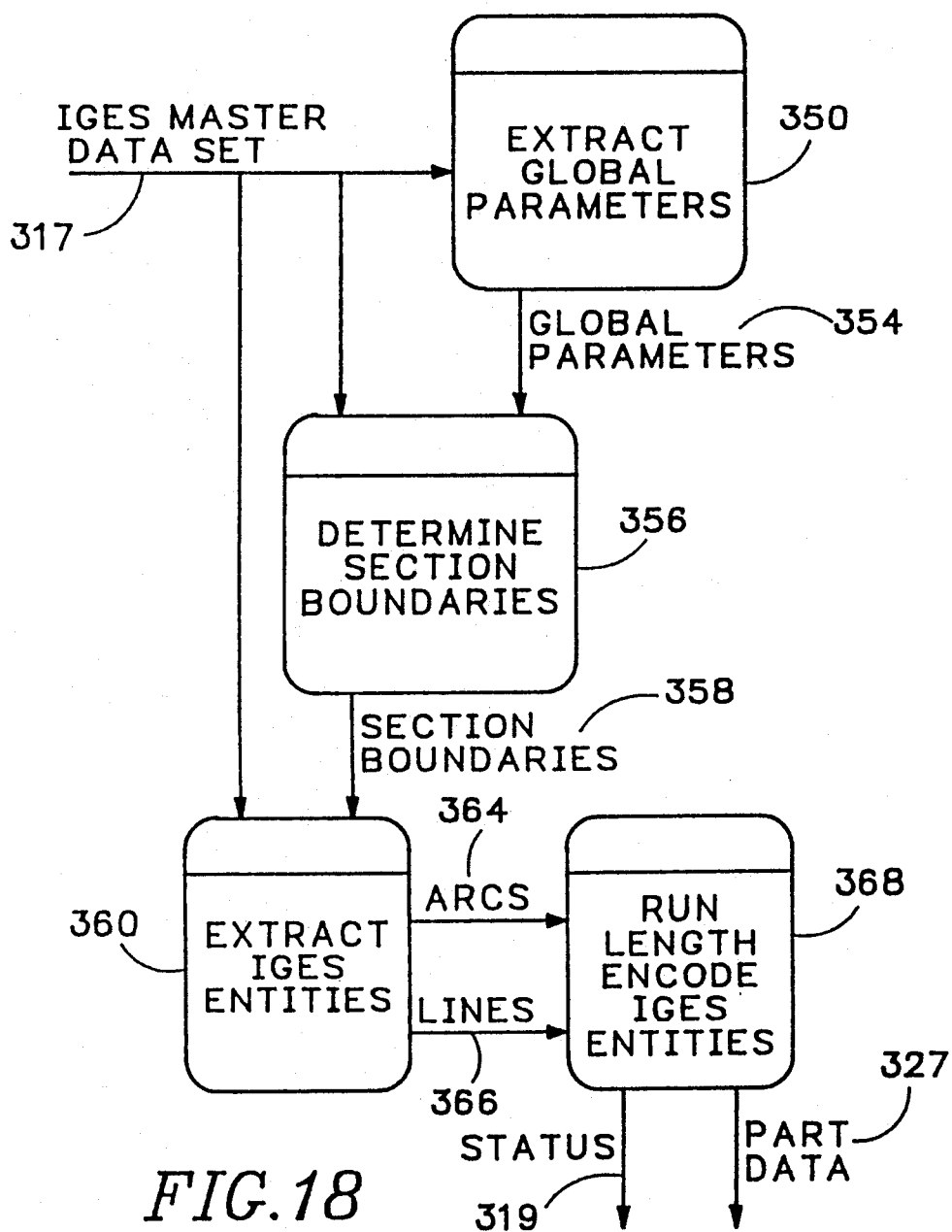
FIG. 18 is a more detailed data flow diagram of the "convert IGES to master" process of FIG. 16.

FIG. 18 illustrates the data flow for the "convert IGES file to part inspection data format" process. The extract global parameters process 350 transforms the IGES master data set data stream 317 into global parameter data stream 354. IGES global parameters contain such items as the name of the author of the file, its date of creation, units of measurement and so on. Global parameter data stream and IGES master data set are fed to the "determine section boundaries" process 356 that provides a section boundary data output stream 358 which defines the boundaries of the various IGES file sections. An IGES format file will be divided into start, global, directory entry, parameter data and terminate sections. The section boundary data stream is fed to the "extract IGES entities" process 360 along with the IGES master data set data stream 317 and produces output data streams, arcs 364 and lines 366. The arcs and lines data streams are fed to the "run length encode IGES" process 368 and a status output data stream 319 and part data output data stream 327 are produced. An IGES format data set is thereby converted to the scan data form to allow comparison with scanned parts.

Figure 19:
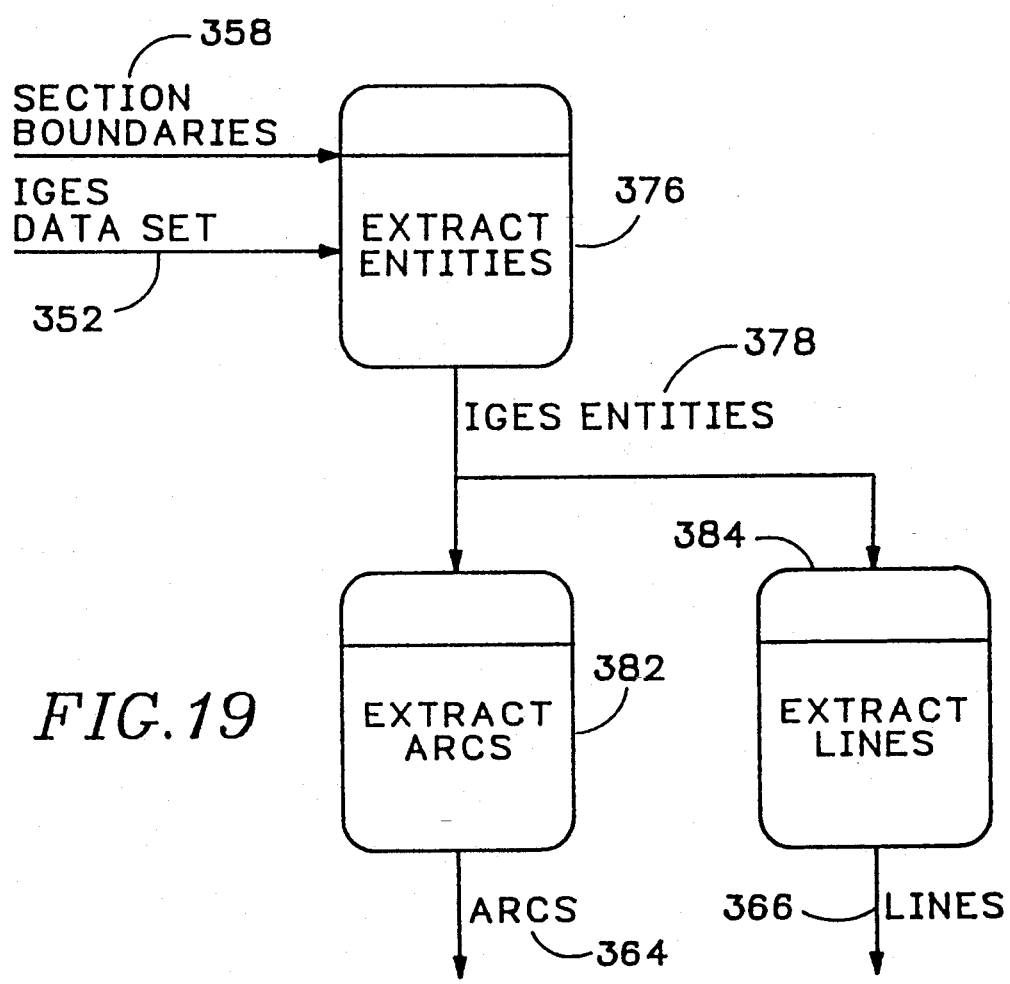
FIG. 19 is a more detailed data flow diagram of the "extract IGES entities" process of FIG. 18.

FIG. 19 is a more detailed data flow diagram of the "extract IGES entity" process block 360 of FIG. 18. The section boundaries 358 and IGES data set 352 data streams are provided to the "extract entities" process at 376 which transforms the input data sets into an IGES entity output data stream 378 and this output data stream is fed to the "extract arcs" process 382 and the "extract lines" process 384. These then produce the output data streams, arcs 364 and lines 366 respectively.

Figure 20:
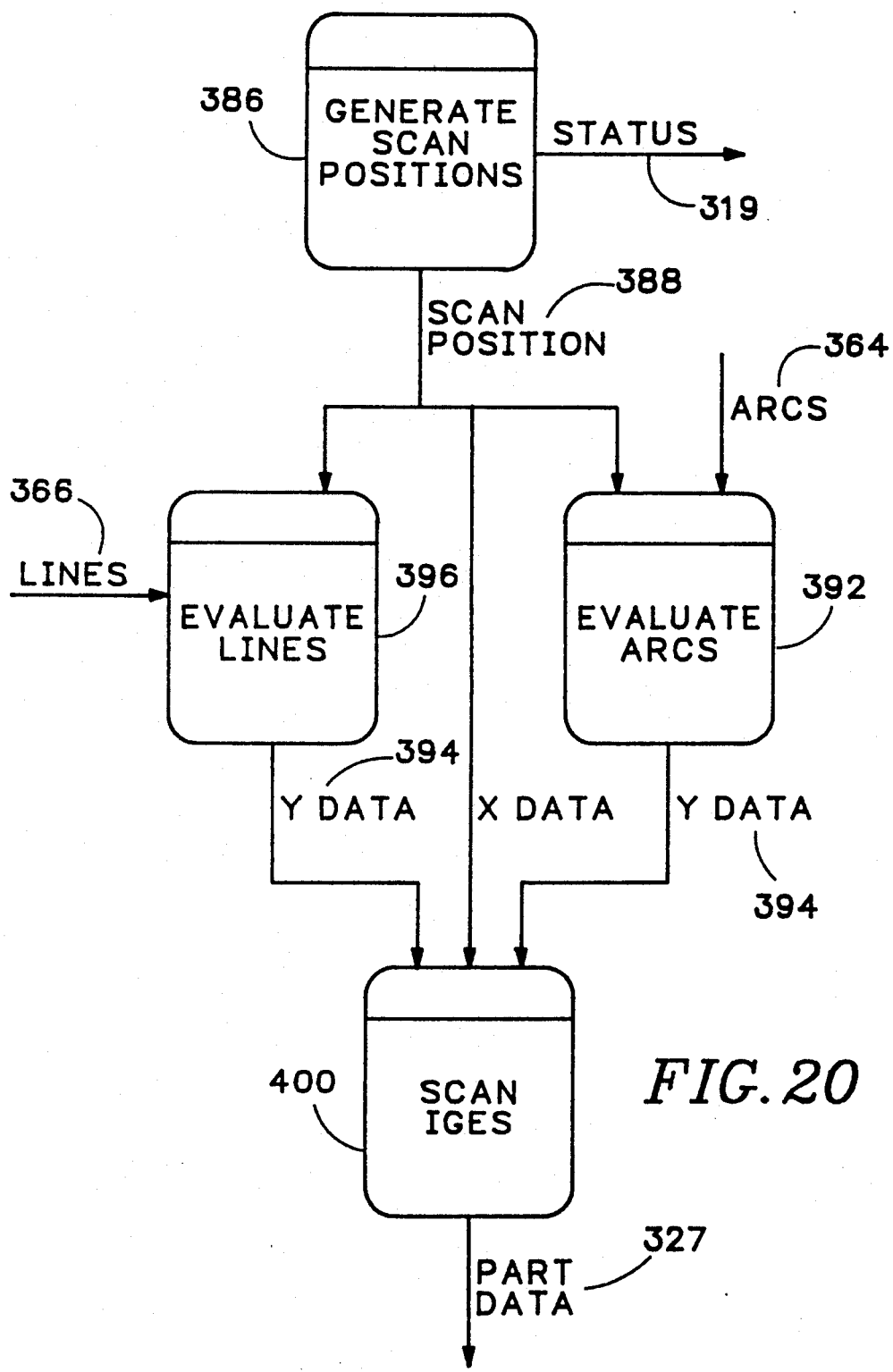
FIG. 20 is a more detailed data flow diagram of the "run length encode IGES entities" process of FIG. 18.

Referring now to FIG. 20, the "run length encode entities" block 368 of FIG. 18 will be described in more detail. "Generate scan positions" process 386 provides status output data stream 319 and scan position 388. The scan position is fed to "evaluate arcs" 392 which also takes the arcs data stream 364 as input, producing Y data stream 394 as output. The scan position data stream (which corresponds to an X value on the X-Y plane) is also provided to "evaluate lines" 396 and this process uses the lines data stream 366 to produce Y data output data stream 394. The Y data streams 394 and scan position (or X data stream) 388 are fed to "scan IGES" 400 which produces part data 327 as an output data stream.

Figure 21:
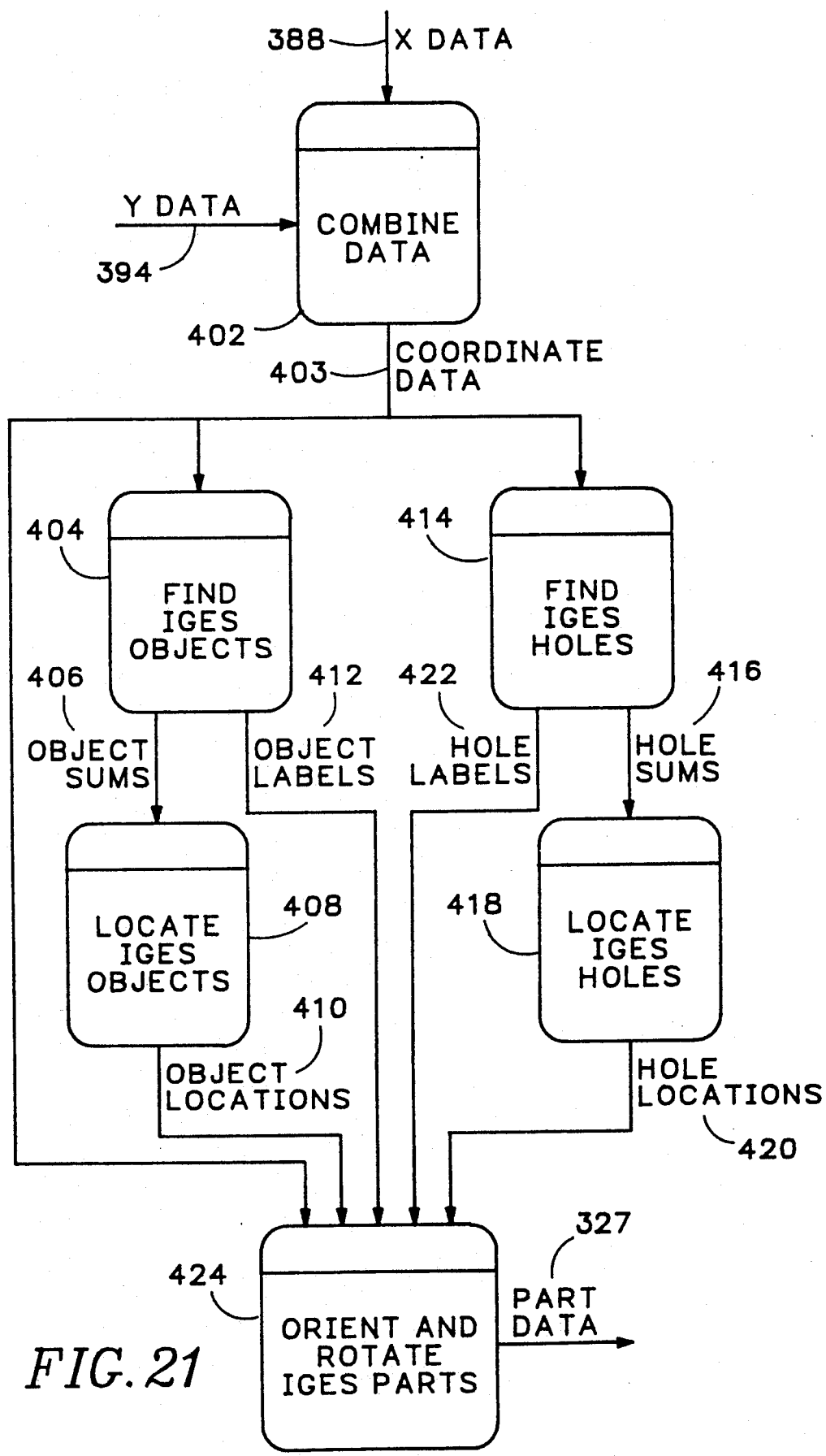
FIG. 21 is an even more detailed data flow diagram of the "scan IGES" function of FIG. 20.

FIG. 21 is a more detailed data flow diagram of "scan IGES" 400 wherein the X data 388 and Y data 394 are input data streams to "combine data" 402 which provides X, Y output coordinate data stream 403 employed by various routines. The "find IGES objects" process 404 uses the coordinate data to supply an object sums output data stream 406, the input data stream to the "locate IGES objects" process 408. An object location output data stream 410 is thereby generated. The "find IGES objects" function 404 also produces an object label data stream 412. The coordinate data 403 is further supplied as input to the "find IGES holes" function 414 which provides a hole sums output data stream 416 input to the "locate IGES holes" function 418. A hole location output data stream 420 is produced. The "find IGES holes" process 414 also provides a hole label output 422. The coordinate data stream 403, the object location data stream 410, the object label data stream 412, the hole label data stream 422 and the hole location data stream 420 are all supplied as input to the "orient and rotate IGES parts" process 424 which transforms the input data streams into a part data output data stream 327. The "find IGES objects" and "find IGES holes" functions operate in a manner corresponding to the functions described herein with reference to the scanning process and FIG. 13.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method for inspecting a part comprising the steps of:
    a) performing a data collection sequence to generate information representative of the part;
    b) determining the major axis, minor axis and angle of orientation of said part;
    c) rotating said representation of said part to a predetermined orientation;
    d) selecting a master part representation corresponding to the part;
    e) comparing said rotated representation with said master part representation to determine whether said part is within a desired tolerance of said master part representation; and
    f) generating an acceptance report based on the results of said step of comparing.

2. The method of claim 1 comprising repeating steps a through f for a plurality of parts.

3. The method of claim 1 wherein said master representation is created from a computer aided design system input.

4. The method of claim 1 wherein said master representation is created by performing steps a through c and storing said representation.

5. The method according to claim 1 wherein said step of comparing said rotated representation with said master part representation comprises the substeps of:
    a) determining whether the periphery of the rotated representation is within a predetermined tolerance of the periphery of said master part representation;
    b) determining whether patterns present in the master part representation are also present in the rotated representation;
    c) determining whether the centers of the patterns in the rotated representation are within a predetermined tolerance of the centers of the corresponding patterns in the master part representation;
    d) determining whether the peripheries of the patterns present in the rotated representation are within a predetermined tolerance of the corresponding patterns in the master part representation; and
    e) determining whether extra patterns not present in the master part representation are present in the rotated representation.

6. The method according to claim 5 wherein said patterns comprise holes.

7. The method according to claim 1 wherein determining the angle of orientation of said part comprises determining moments of said part and determining the angle of orientation as a function of said moments.

8. The method according to claim 1 wherein said step of selecting a master part representation corresponding to the part comprises the substeps of:
    a) determining a part identification based on the information representative of the part, said identification based on physical parameters of the part; and
    b) retrieving a master part representation from a database of master parts, said retrieved master part representation having a part identification similar to said determined part identification.

9. The method according to claim 8 wherein said step of determining a part identification comprises determining a weighted sum of a set of dimensional parameters of the part.

10. The method of claim 1 wherein said step of generating an acceptance report comprise the substeps of:
    a) displaying a scanned part; and
    b) displaying the difference between the scanned part and a master part.

11. A method for inspecting a sheet metal part comprising the steps of:
    a) performing a data collection sequence to generate information representative of the sheet metal part;
    b) determining the major axis, minor axis and angle of orientation of said part;
    c) rotating said representation of said part to a predetermined orientation;
    d) selecting a master part representation corresponding to the sheet metal part;
    e) comparing said rotated representation with said master part representation; and
    f) generating an acceptance report based on the results of said step of comparing, wherein said step of generating an acceptance report comprises the substeps of:
        1) displaying a scanned part;
        2) displaying the difference between the scanned part and a master part, and
        3) indicating the pass/fail status of the scanned part.

12. Apparatus for inspecting parts for conformance with a desired template, comprising:
    storage means for storing information representative of the exterior peripheral measurements and interior hole peripheral measurements and placements of the desired template;
    data collection means for linearly scanning a part and generating information representative of the orientation and exterior peripheral measurements and interior hole peripheral measurements and placements of the scanned part;
    comparison means for comparing the information representative of the actual exterior peripheral measurements and interior hole peripheral measurements and placements of the scanned part with the information representative of the exterior peripheral measurements and interior hole peripheral measurements and placements of the desired template irrespective of the orientation of the part; and
    means for reporting comparison results generated by said comparison means.

13. Apparatus according to claim 12 wherein said data collection means comprises an optical scanner and a translation table, said translation table moving the scanned part along an axis normal to the optical scanner.

14. Apparatus according to claim 12 wherein said data collection means comprises at least one video camera oriented in a direction normal to the plane of the scanned part for providing Y-axis information regarding the part, and a translation table for relative translation of the scanned part across the field of view of said at least one video camera for providing X-axis information about the part.

15. Apparatus according to claim 12 wherein said information representative of the exterior peripheral measurements and interior hole peripheral measurements and placements of the desired template comprises a stored digital representation of a master part.

16. Apparatus according to claim 15 wherein said digital representation of a master part is generated by a computer aided design process.

17. Apparatus according to claim 15 wherein said digital representation of a master part is generated by scanning a master part with said apparatus.

18. Apparatus according to claim 12 further comprising selection means for selecting a desired template from a plurality of stored templates.

19. Apparatus according to claim 12 further comprising selection means responsive to data gathered by said data collection means for selecting an appropriate desired template from a plurality of stored templates.

20. A system for inspecting sheet metal parts comprising:
 a database of a plurality of data sets representative of a plurality of inspection templates;
 an examination surface upon which parts to be inspected are placed;
 lighting means disposed in relation to a first side of the examination surface;
 vision means mounted in relation to a second side of said examination surface;
 drive means for bringing about relative motion between the examination surface and the vision means along an axis; and
 means responsive to said vision means for generating a first data set wherein said first data set is representative of an inspected part, for selecting a second data set from said database wherein said second data set is representative of an inspection template, and for comparing said first and second data sets to determine if said first data set is within a predetermined tolerance relative to said second data set.

21. The system according to claim 20 further comprising:
 means for conveying information about said first data set, said second data set and an acceptance status of said inspected part.

22. The system according to claim 21 wherein said information conveying means comprises a computer graphics display terminal.

23. The system according to claim 20 wherein said second data set is in digital form.

24. The system according to claim 20 wherein said responsive means comparing said first and second data sets defines the difference between said data sets.

25. The system according to claim 20 wherein said responsive means generates a plurality of data sets representative of a plurality of inspected parts, selects a plurality of second data sets from said database, each of said second data sets being representative of an inspection template corresponding to at least one of said plurality of first data sets, and compares each of said second data sets with at least one of said first data sets to determine if said at least one of said first data sets is within a predetermined tolerance relative to a said second data set.

* * * * *